(12) United States Patent  
Davis et al.

(10) Patent No.: US 12,059,264 B2  
(45) Date of Patent: Aug. 13, 2024

(54) SYSTEMS AND METHODS FOR TREMOR DETECTION AND QUANTIFICATION

(71) Applicant: Linus Health, Inc., Waltham, MA (US)

(72) Inventors: Randall Davis, Weston, MA (US); Catherine Medlock, Lexington, MA (US); Bruce Musicus, Lexington, MA (US); Alan V. Oppenheim, Cambridge, MA (US); Dana L. Penney, Weston, MA (US); William A. Souillard-Mandar, Cambridge, MA (US)

(73) Assignee: LINUS HEALTH, INC., Waltham, MA (US)

( * ) Notice: Subject to any disclaimer, the term of this patent is extended or adjusted under 35 U.S.C. 154(b) by 81 days.

(21) Appl. No.: 17/221,529

(22) Filed: Apr. 2, 2021

(65) Prior Publication Data

US 2022/0054077 A1    Feb. 24, 2022

Related U.S. Application Data

(63) Continuation of application No. 16/124,689, filed on Sep. 7, 2018, now abandoned.
(Continued)

(51) Int. Cl.
*A61B 5/00* (2006.01)
*A61B 5/11* (2006.01)
(Continued)

(52) U.S. Cl.
CPC .......... *A61B 5/4088* (2013.01); *A61B 5/1101* (2013.01); *A61B 5/1124* (2013.01);
(Continued)

(58) Field of Classification Search
None
See application file for complete search history.

(56) References Cited

U.S. PATENT DOCUMENTS

| 5,562,104 A | 10/1996 | Hochberg et al. |
| 6,454,706 B1 | 9/2002 | Pullman |

(Continued)

FOREIGN PATENT DOCUMENTS

| CN | 103315744 B | 10/2014 |

OTHER PUBLICATIONS

C. P. Prinsloo and P. J. Cilliers, "Measurement and analysis of muscle tremor using a digitising tablet," IEEE International Symposium on Industrial Electronics. Proceedings. ISIE'98 (Cat. No.98TH8357), 1998, pp. 335-338 vol.1, doi: 10.1109/ISIE.1998.707803. (Year: 1998).*

(Continued)

*Primary Examiner* — Benjamin S Melhus
(74) *Attorney, Agent, or Firm* — Bookoff McAndrews, PLLC

(57) ABSTRACT

Systems and methods are disclosed for detecting tremors in a subject. One method comprises receiving data from a digital device, the data comprising a plurality of digital device positions and a plurality of timestamps, each timestamp in the plurality of timestamps being associated with a digital device position in the plurality of digital device positions. The method further comprises determining a plurality of frequencies of hand movements of the subject based on the plurality of digital device positions and plurality of timestamps. The method further comprises determining a subportion of the data corresponding to frequencies of hand movements above a low tremor threshold, and determining a magnitude of tremors of the subject's hand based, at least in part, on the subportion of the data.

22 Claims, 24 Drawing Sheets

Related U.S. Application Data

(60) Provisional application No. 62/555,940, filed on Sep. 8, 2017.

(51) Int. Cl.

| | | |
|---|---|---|
| *G06F 3/0354* | (2013.01) | |
| *G06F 3/0488* | (2022.01) | |
| *G06F 3/04883* | (2022.01) | |
| *G16H 50/20* | (2018.01) | |
| *H04L 67/02* | (2022.01) | |
| *H04L 67/06* | (2022.01) | |

(52) U.S. Cl.
CPC .......... *A61B 5/725* (2013.01); *G06F 3/03545* (2013.01); *G06F 3/04883* (2013.01); *G16H 50/20* (2018.01); *A61B 2562/0219* (2013.01); *H04L 67/02* (2013.01); *H04L 67/06* (2013.01)

(56) References Cited

U.S. PATENT DOCUMENTS

| | | | | |
|---|---|---|---|---|
| 6,546,134 | B1* | 4/2003 | Shrairman | A61B 5/1104 |
| | | | | 382/187 |
| 9,289,603 | B1 | 3/2016 | Giuffrida | |
| 9,672,618 | B1* | 6/2017 | Hassanain | G16H 50/20 |
| 10,383,553 | B1* | 8/2019 | Glenn | A61B 5/16 |
| 2005/0053269 | A1* | 3/2005 | Franke | A61B 5/00 |
| | | | | 600/595 |
| 2005/0243061 | A1 | 11/2005 | Liberty | |
| 2006/0122472 | A1* | 6/2006 | Pullman | A61B 5/16 |
| | | | | 600/300 |
| 2010/0152622 | A1 | 6/2010 | Teulings | |
| 2011/0054361 | A1 | 3/2011 | Sakoda | |
| 2012/0330182 | A1* | 12/2012 | Alberts | G16H 50/30 |
| | | | | 607/45 |
| 2014/0031724 | A1 | 1/2014 | Davis | |
| 2014/0074267 | A1* | 3/2014 | Alberts | G16H 50/20 |
| | | | | 700/92 |
| 2016/0128621 | A1* | 5/2016 | Machado | A61B 5/1101 |
| | | | | 600/595 |
| 2017/0296101 | A1* | 10/2017 | Alberts | A61B 5/1116 |
| 2017/0340261 | A1 | 11/2017 | Torres | |
| 2018/0353105 | A1* | 12/2018 | Davis | A61B 5/16 |

OTHER PUBLICATIONS

J. Kim, C. Parnell, T. Wichmann and S. P. DeWeerth, "Quantitative assessment of arm tremor in people with neurological disorders," 2016 38th Annual International Conference of the IEEE Engineering in Medicine and Biology Society (EMBC), 2016, pp. 2299-2302, doi: 10.1109/EMBC.2016.7591189. (Year: 2016).*

Müller, Stephan, et al. "Increased diagnostic accuracy of digital vs. conventional clock drawing test for discrimination of patients in the early course of Alzheimer's disease from cognitively healthy individuals." Frontiers in aging neuroscience 9 (2017): 101. (Year: 2017).*

A. Berit and O. Dehlin, "The Clock-Drawing Test," Age and Ageing, vol. 27, No. 3, pp. 399-404, 1998.

W. Souillard-Mandar, R. Davis, C. Rudin, R. Au, D. J. Libon, R. Swenson, C. C. Price, M. Lamar and D. L. Penney, "Learning Classification Models of Cognitive Conditions from Subtle Behaviors in the Digital Clock Drawing Test," Machine Learning, vol. 102, No. 3, pp. 393-441, 2016.

T. Eichorn, T. Gasser, N. Mai, C. Marquardt, G. Arnold, J. Schwarz and W. Oertel, "Computational Analysis of Open Loop Handwriting Movements in Parkinson's Disease: a Rapid Method to Detect Dopamimetic Effects," Movement Disorders, vol. 11, No. 3, pp. 289-297, 1996.

D. Haubenberger, D. Kalowitz, F. B. Nahab, C. Toro, D. Ippolito, D. A. Luckenbaugh, L. Wittevrongel and M. Hallett, "Validation of Digital Spiral Analysis as Outcome Parameter for Clinical Trials in Essential Tremor," Movement Disorders, vol. 26, No. 11, pp. 2073-2080, 2011.

A. U"nlu", R. Brause and K. Krakow, "Handwriting Analysis for Diagnosis and Prognosis of Parkinson's Disease," in International Symposium on Biological and Medical Data Analysis, 2006.

F. Miralles, S. Tarongi and A. Espino, "Quantification of the Drawing of an Archimedes Spiral Through the Analysis of its Digitized Picture," Journal of Neuroscience Methods, vol. 152, No. 1, pp. 18-31, 2006.

N. Zhi, B. K. Jaeger, A. Gouldstone, S. Frank and R. Sipahi, "A Novel Quantitative Assessment Method to Detect Effects of Essential Tremor on Static Handwriting," in 2015 41st Annual Northeast Biomedical Engineering Conference (NEBEC), 2015.

G. Grimaldi and M. Manto, "Neurological Tremor: Sensors, Signal Processing and Emerging Applications," Sensors, vol. 10, No. 2, pp. 1399-1422, 2010.

S. L. Pullman, "Spiral Analysis: a New Technique for Measuring Tremor with a Digitizing Tablet, " Movement Disorders, vol. 13, No. S3, pp. 85-89, 1998.

M. Memedi, A. Sadikov, V. Groznik, J. Zabkar, M. Mozina, F. Bergquist, A. Johansson, D. Haubenberger and D. Nyholm, "Automatic Spiral Analysis for Objective Assessment of Motor Symptoms in Parkinson's Disease," Sensors, vol. 15, No. 9, pp. 23727-23744, 2015.

S. Patel, K. Lorincz, R. Hughes, N. Huggins, J. Growdon, D. Standaert, M. Akay, J. Dy, M. Welsh and P. Bonato, "Monitoring Motor Fluctuations in Patients with Parkinson's Disease Using Wearable Sensors," IEEE Transactions on Information Technology in Biomedicine, vol. 13, No. 6, pp. 864-873, 2009.

R. J. Elble and et al, "Tremor Amplitude is Logarithmically Related to 4- and 5-Point Tremor Rating Scales," Brain, vol. 129, No. 10, pp. 2660-2666, 2006.

"Digital Cognition Technologies," [Online]. Available: http://www.digitalcognitiontechnologies.com.

R. Davis, D. J. Libon, R. Au, D. Pitman and D. L. Penney, "Think: Inferring Cognitive Status from Subtle Behaviors," in Proceedings of the AAAI Conference on Artificial Intelligence, 2014.

H.-L. Teulings and F. J. Maarse, "Digital Recording and Processing of Handwriting Movements," Human Movement Science, vol. 3, No. 1-2, pp. 193-217, 1984.

J. Jankovic, "Parkinson's Disease: Clinical Features and Diagnosis," Journal of Neurology, Neurosurgery & Psychiatry, vol. 79, No. 4, pp. 368-376, 2008.

E. D. Louis and et al., "Validity and Test-Retest Reliability of a Disability Questionnaire for Essential Tremor," Movement Disorders, vol. 15, No. 3, pp. 516-523, 2000.

P. B. Bain and et al, "Assessing Tremor Severity," Journal of Neurology, Neurosurgery & Psychiatry, vol. 56, No. 8, pp. 868-873, 1993.

Andre Pierre Legrand et al: "New Insight in spiral drawing analysis methods—Application to action tremor quantification", Clinical Neurophysiology, Elsevier Science, IE, vol. 128, No. 10, Jul. 17, 2017, pp. 1823-1834.

Camilo Toro: "NeuroGlyphics Manual", Jan. 1, 2016, retrieved from the Internet: URL:http://www.neuroglyphics.org/Download.aspx.

* cited by examiner

400

2100

SYSTEMS AND METHODS FOR TREMOR DETECTION AND QUANTIFICATION

CROSS-REFERENCE TO RELATED APPLICATION(S)

This application is a continuation application of U.S. Nonprovisional patent application Ser. No. 16/124,689 filed Sep. 7, 2018, which claims the benefit of priority from U.S. Provisional Patent Application No. 62/555,940, filed Sep. 8, 2017, each of which is incorporated herein by reference in its entirety.

FIELD OF THE DISCLOSURE

Various embodiments of the present disclosure relate generally to cognitive assessment and tremor measurement. More specifically, particular embodiments of the present disclosure relate to systems and methods for detecting tremors in a patient using the same data that is used for cognitive assessment. Other embodiments may detect only tremor.

BACKGROUND

The Clock Drawing Test (CDT) is used as a way of determining an individual's cognitive status, such as healthy or with cognitive impairments. Impairments may include memory impairment disorders, vascular cognitive disorders, and Parkinson's disease, for example. The CDT may be given as follows: the individual is asked to draw, on a piece of paper, a clock containing a clockface and all the digits, showing a time such as ten past eleven (the Command clock). The individual is then asked to copy a printed clock showing the same time (the Copy clock).

Traditional tremor measuring drawing tests are hand-scored by clinicians. As a result, existing widely accepted tremor measurement scales are based only on quantities that can be measured with the naked eye. Given the coarseness of subjective visual judgments, a one-point increase in the tremor score assigned using the Fahn-Tolosa-Marin scale, for example, may correspond to an increase in tremor amplitude—as measured by an accelerometer—by as much as a factor of two.

The foregoing general description and the following detailed description are exemplary and explanatory only and are not restrictive of the disclosure.

SUMMARY

According to certain aspects of the present disclosure, systems and methods are disclosed for tremor detection and quantification, which may be used in combination to gauge cognitive impairment. As will be discussed herein, in at least certain embodiments of the present disclosure, quantitative measurement of tremor utilizing sophisticated signal processing and/or machine learning technology may provide more precise identification of tremor than subjective human scoring.

One method comprises receiving data from a digital device, the data comprising a plurality of digital device positions and a plurality of timestamps, each timestamp in the plurality of timestamps being associated with a digital device position in the plurality of digital device positions. The method further comprises determining a plurality of frequencies of hand movements of the subject based on the plurality of digital device positions and plurality of timestamps. The method further comprises determining a subportion of the data corresponding to frequencies of hand movements above a low tremor threshold, and determining a magnitude of tremors of the subject's hand based, at least in part, on the subportion of the data.

In accordance with another embodiment, a system for detecting tremors in a subject comprises: a data storage device storing instructions for detecting tremors in a subject; and a processor configured to execute a method comprising: receiving data from a digital device, the data comprising a plurality of digital device positions and a plurality of timestamps, each timestamp in the plurality of timestamps being associated with a digital device position in the plurality of digital device positions. The method further comprises determining a plurality of frequencies of hand movements of the subject based on the plurality of digital device positions and plurality of timestamps. The method further comprises determining a subportion of the data corresponding to frequencies of hand movements above a low tremor threshold, and determining a magnitude of tremors of the subject's hand based, at least in part, on the subportion of the data.

In accordance with another embodiment, a non-transitory computer readable medium for use on a computer system containing computer-executable programming instructions for performing a method of detecting tremors in a subject, the method comprising: receiving data from a digital device, the data comprising a plurality of digital device positions and a plurality of timestamps, each timestamp in the plurality of timestamps being associated with a digital device position in the plurality of digital device positions. The method further comprises determining a plurality of frequencies of hand movements of the subject based on the plurality of digital device positions and plurality of timestamps. The method further comprises determining a subportion of the data corresponding to frequencies of hand movements above a low tremor threshold, and determining a magnitude of tremors of the subject's hand based, at least in part, on the subportion of the data.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Figure 1:
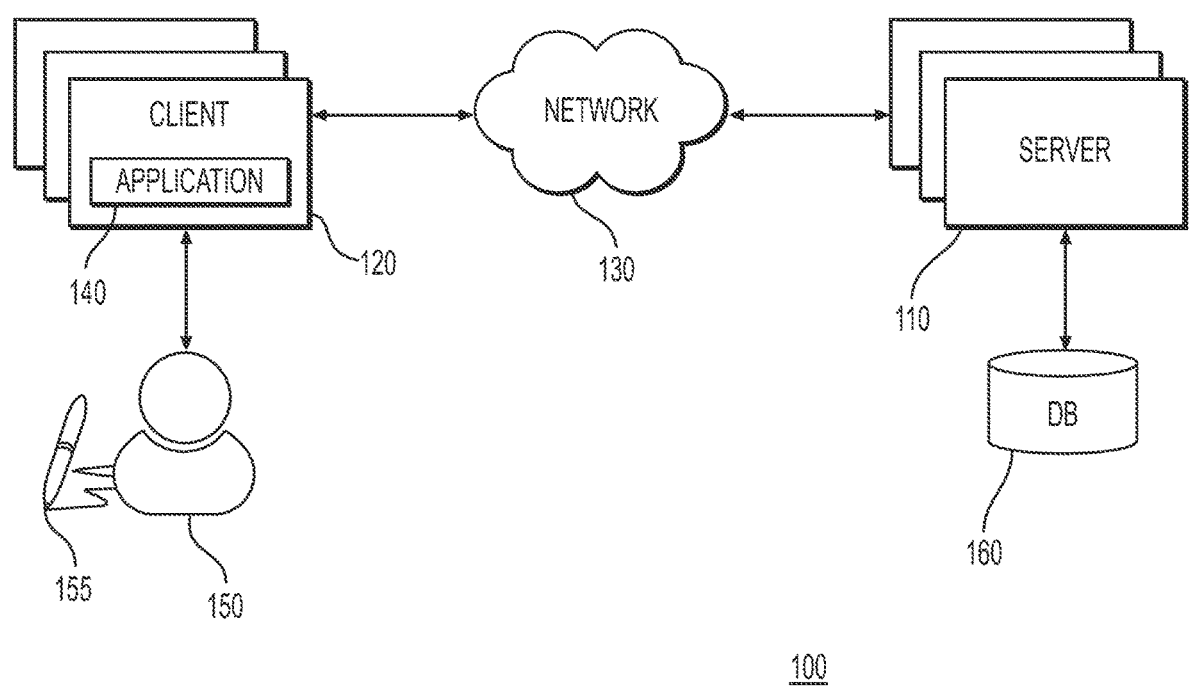
FIG. 1 is a high-level block diagram illustrating an example system for detecting tremor in patients in accordance with techniques presented herein.

Reference will now be made in detail to the exemplary embodiments of the disclosure, examples of which are illustrated in the accompanying drawings. Wherever possible, the same reference numbers will be used throughout the drawings to refer to the same or like parts.

This application discloses systems and techniques for detection and/or quantification of patient tremor, possibly in conjunction with screening or diagnosing cognitive impairment. One embodiment may require a subject to draw, for example, a clock using a digitizing pen, although other drawing, writing, and pen stroke capture techniques may be utilized. Some tests may ask the subject to follow a template spiral or other assigned pattern while holding his/her arm off the table, while other tests disclosed herein, such as the digital Clock Drawing Test, may allow the subject to hold the pen comfortably and write freehand on a sheet of paper.

Features derived from the recorded data may be processed by algorithms into scores that correlate with different types of cognitive impairment. Cognitive impairment can be inferred by incorrect positioning or omission of clock digits, incorrect positioning or omission of the clock hands, and so forth. Techniques may further include using a digitizing pen that records its position on the page as a function of time. Many more features can be accurately measured in this manner, such as pauses between drawing different portions of the clockface, timing of strokes, precise positioning of features relative to the nominal center of the drawing, and so forth. Using the digital clock test data, classifiers may be created that function either as screening or diagnostic tests for multiple types of cognitive impairment.

Another neurological disorder that may be monitored is tremor, especially as this is often associated with serious medical conditions such as Parkinson's disease. Some methods of measuring tremor may require subjects to draw spirals, loops, or cursive letters, or use a biomedical sensor such as an accelerometer.

Traditional tremor measuring drawing tests are hand-scored by clinicians. As a result, existing widely accepted tremor measurement scales are based only on quantities that can be measured with the naked eye. Given the coarseness of subjective visual judgments, a one-point increase in the tremor score assigned using the Fahn-Tolosa-Marin scale, for example, may correspond to an increase in tremor amplitude—as measured by an accelerometer—by as much as a factor of two. Techniques presented herein that instrument a tremor measurement drawing task with a digital pen can improve on the precision of the measurement of mild as well as large tremors.

Thus, in at least certain embodiments of this disclosure, novel systems and methods instrument a digital drawing test intended for screening or diagnosing neurological impairment, such as a Digital Clock Drawing Test, and re-use all or a portion of the recorded data to measure tremor as well. This avoids having to present the patient with two separate tests, which speeds up the testing procedure, while delivering useful scores for both cognitive impairment as well as tremor severity. The tremor test can also be administered by itself, as techniques presented herein may require relatively little patient time or effort, and yet produces tremor ratings that correlate well with ratings by medical professionals.

In addition, the present analysis, according to exemplary embodiments, may derive low-pass, bandpass velocity, and bandpass acceleration measures and components of those entities in specific directions, possibly related to the direction of pen motion, any of which may be derived from one or more pen strokes within the drawing (for example, the "clockface" circle). These measures may be used to compute several robust tremor quantification features that correlate strongly with tremor. Although the Digital Clock Test is described in connection with many of the embodiments, other types of tests and drawings may be used and fall within the scope of the inventions.

On a particular subset of labeled data from subjects diagnosed as either "Healthy" or "Essential Tremor," receiver operating characteristic (ROC) curves were produced with area under the curve (AUC) values above 0.97. (AUC is a quality measure with a range from 0.5 (poor) to 1.0 (perfect)). Feature scores agree well with medical neurologist movement disorder specialists who examined the same selected set of pen strokes, and agreement between specialists and features scores remains even when the raters are allowed to examine the entire clock drawing, not just the enclosing clockface circle. These algorithms and metrics produce results that are highly correlated with, or superior to, clinician judgment, and allow for the detection and differentiation of various conditions, such as distinguishing Healthy from Essential Tremor, a disorder that causes involuntary and rhythmic shaking.

Referring now to the figures, FIG. 1 is a high-level block diagram of a computing environment 100 for detecting tremors in patients according to one embodiment. The computing environment 100 may include one or more servers 110, and any number of client devices 120. The servers 110 and/or client devices 120 may be communicatively coupled by an electronic network 130, such as the Internet. In one embodiment, the one or more servers 110 may be web servers, and an application 140 may execute one or more techniques presented herein via a web browser. In another embodiment, the servers 110 may be application servers that provide an instance of one or more applications 140 to the client device 120. In another embodiment, the servers 110 may provide data, for example from a data store 160, to support the execution of the one or more applications 140 on the client device 120. In yet another embodiment, application 140 may be installed on client device 120, and may operate without communication with the one or more servers 110. In embodiments discussed herein, a tremor feature may be calculated using a server 110 in the cloud 130. This tremor feature may be calculated in a computer 140 attached with a wire or wirelessly to the digital device 155. This tremor feature may also be calculated on the digital device 155 itself, in accordance with techniques presented herein.

In some embodiments, patient and other data may be utilized from data store 160, which may be connected to server 110 and/or client device 120. The client device 120 is a computer or other electronic device which may be used by one or more users 150 to perform activities which may include browsing web pages on the network 130, or using the one or more applications 140. The client device 120, for example, may be a personal computer, personal digital assistant (PDA), a mobile telephone, tablet, or another type of electronic device. Only one server 110, and one client device 120 will typically be discussed herein to simplify the description. However, portions of techniques discussed herein may be executed on different servers 110 and client devices 120.

The network 130 represents the communication pathways between (e.g., communicative coupling of) the server 110 and client device 120. In one embodiment, the network 130 is the Internet. The network 130 may also include dedicated or private communications links that are not necessarily a part of the Internet. In one embodiment, the network 130 uses various communications technologies and/or protocols. Thus, the network 130 may include links using technologies such as Ethernet, 802.11, integrated services digital network (ISDN), digital subscriber line (DSL), asynchronous transfer mode (ATM), application programming interface (API), etc. It may also include wireless links such as WiFi or Bluetooth, or be a wired connection. Similarly, the networking protocols used on the network 130 may include the transmission control protocol/Internet protocol (TCP/IP), the hypertext transport protocol (HTTP), the simple mail transfer protocol (SMTP), the file transfer protocol (FTP), etc. The data exchanged over the network 130 can be represented using technologies and/or formats including the hypertext markup language (HTML), the extensible markup language (XML), etc. In addition, all or some of links may be encrypted using encryption technologies such as the secure sockets layer (SSL), transport layer security (TLS), secure HTTP (HTTPS), and/or virtual private networks (VPNs). In another embodiment, the entities may use custom and/or dedicated data communications technologies instead of, or in addition to, the ones described above.

As shown in FIG. 1, client device 120 may execute an application 140, such as a desktop application, web application, or browser application, that allows a user to retrieve and view content stored on other computers or servers on the network 130. The application 140 may also allow the user to submit information to other computers on the network 130, such as through user interfaces, web pages, application program interfaces (APIs), and/or other data portals. In one embodiment, the application 140 is a web browser, such as MICROSOFT INTERNET EXPLORER or MOZILLA FIREFOX. The application 140 may support technologies including JavaScript, ActionScript, and other scripting languages that allow the client device 120 to perform actions in response to scripts and other data sent to the application via the network 130. In some embodiments, functions ascribed herein to the application 140 are implemented via plug-ins such as ADOBE FLASH.

The server 110 may deliver data associated with a user interface, such as a web page, to the application 140 over the network 130. The application 140 may then load the user interface and present it to the user.

Techniques presented herein may provide a tool for detecting tremor in patients. These techniques may be presented on one or more user interfaces. Certain techniques discussed herein may be presented to patients 150, others to clinicians such as physicians, etc. These features may have associated security requirements before they may be used. For example, different subjects/patients/clinicians/users 150 of the application 140 may have different levels of privileges, allowing them to access differing features of the application. In addition, many steps of techniques discussed herein are disclosed in a particular order. In general, steps discussed may be performed in any order, unless expressly stated otherwise.

Techniques described herein may use a database 160 of many, for example thousands, of subjects who have taken the digital clock test, and who may have been diagnosed with one or more of a variety of neurological problems. Some subjects in the database 160 may be used as healthy controls. In each digital clock or other drawing test, the subject 160 may draw the Command and Copy clocks using a digital device 155 (may be referred to herein as a digital pen, but may also comprise a stylus, device tracking finger movements on a touchpad, computer mouse tracking device, gesture tracking device, subject movement tracking software installed on a generic computing device, etc.) or other device that allows the recording of pen strokes. Such a digital pen 155 may record the position of the pen point on the page, for example, dozens of times per second (such as 75 times per second) with accuracy of a small fraction of the drawing size in the x- and y-directions (for example, 0.05 mm).

The system may record the drawing as a series of strokes corresponding to samples of pen position in time while it was pressed on the paper. The pen 155 may record the $(x[n], y[n])$ coordinates of the position of the $n^{th}$ sample together with, for example, a timestamp $t[n]$ and/or pressure $p[n]$ for each time sample. Some pens may be able to record angle and rotation as well. Other coordinate frames, such as polar, may be used, and the sampling rate need not be uniform. A stroke classification algorithm may assign each stroke to one of several predefined symbol types. In one embodiment, only the stroke identified as the "clockface" outline might be used in the tremor test. This is the circle that is supposed to mark the boundary of the clock, and be big enough to hold all the digits and the hands. Characteristics of this strategy include that the clockface outline may be drawn free-hand, may be the longest stroke, and may typically take 2-4 seconds or more to draw, so there is time for tremor to manifest itself. It may be helpful that the shape is a circle, which forces the writer to move the pen 155 through all directions, forcing multiple muscles to try to guide the pen 155 through a variety of hand positions. At the same time, the shape has no sharp corners so a healthy person (or unhealthy) should not need to make sudden high-speed changes in velocity or acceleration.

Figure 2:
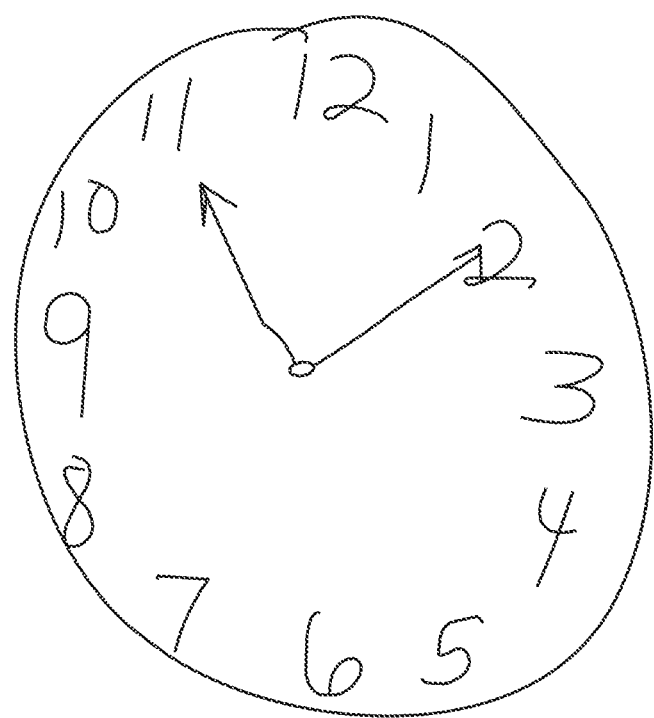
FIG. 2 is an example drawing of a clockface drawn by a healthy patient.

FIG. 2 is an example of a complete clock drawing 200 from a healthy subject, while FIGS. 3A-3D show analyses of the stroke identified as the clockface outline from FIG. 2. The original clockface of FIG. 2 may be somewhat circular or elliptical. Sometimes the subject may use multiple strokes to finish the outline. In some embodiments only the single longest stroke may be used, while in others one or more of the strokes in the outline may be used, and yet other embodiments may choose to analyze other clock components such as the hour and minutes hands. In general, tremor tends to oscillate in the range of 4-8 Hz, and so accurate results may be achieved by using the longer strokes in the drawing that take one or more seconds to draw.

A possible first step in processing digitized pen positions is to derive a pen path in x,y coordinates as a function of time with samples interpolated at a uniform rate. For example, some digitizing devices may omit intermediate samples if the path is straight and can be predicted from samples at the start and end of a segment. Other devices may change the sampling rate depending on pen speed. In any case, it is helpful (though not necessarily required) to interpolate the pen position to an (x[n],y[n]) path uniformly sampled in time n.

Figure 3A:
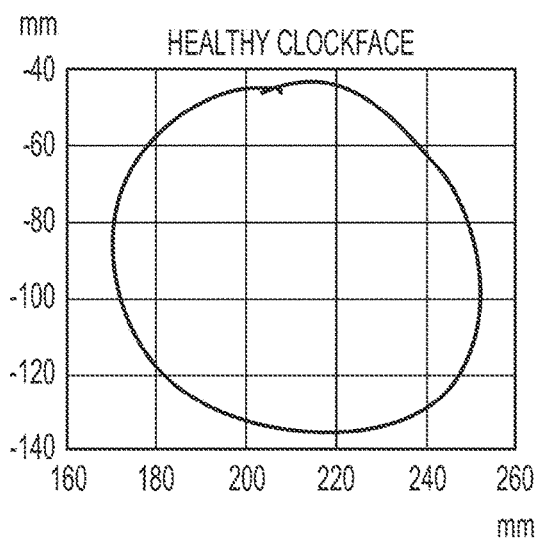
FIGS. 3A-3D depict example metrics corresponding to the drawing of a clockface.
Figure 3B:
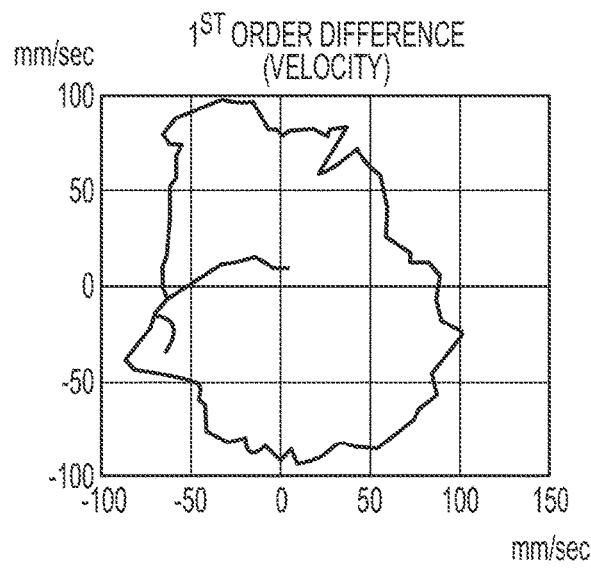
Figure 3C:
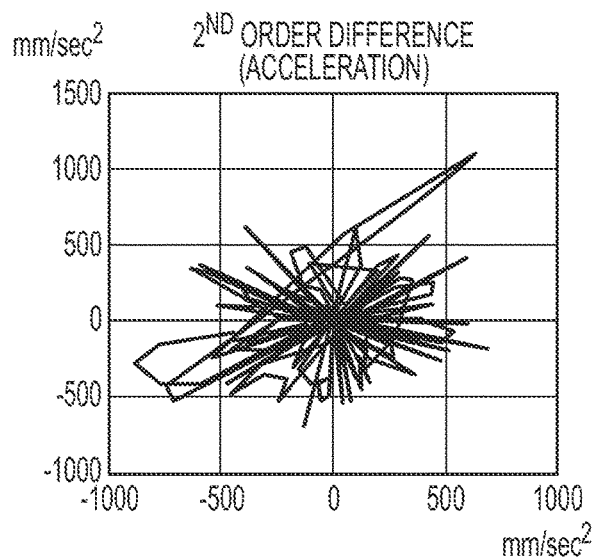
Figure 3D:
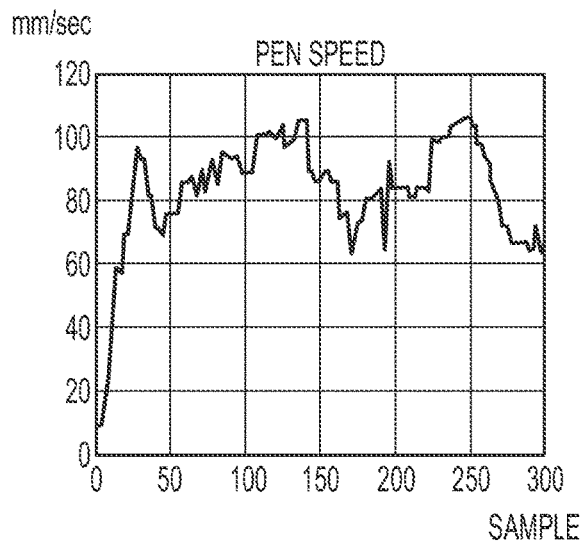

The next step may compute first and second order vector differences between successive samples, which can be viewed as initial estimates of pen velocity and acceleration in two dimensions. FIG. 3A shows an example clockface circle drawn by a healthy individual. FIGS. 3B and 3C show example unfiltered first and second order vector differences between successive samples. Each sample on the line in the graph corresponds to first or second order (x,y) differences, at different moments in time. FIG. 3B with first-order differences is a simple estimate of pen velocity, and FIG. 3C with second-order differences is a simple estimate of pen acceleration. Other signal processing techniques that we discuss later may also be used to estimate velocity and acceleration. In FIGS. 3B and 3C, distance from the origin corresponds to the magnitude of pen velocity and acceleration, respectively, while the angle relative to the origin indicates the direction of the pen velocity and acceleration at a moment in time. FIG. 3D plots the magnitude of the first order vector difference (pen velocity) as a function of sample (time). If the patient had perfect drawing ability, FIG. 3A would show a perfect circle, and velocity graph FIG. 3D would show constant velocity over time, perhaps with start and stop transients at the ends. FIG. 3B would be a perfect circle assuming drawing velocity (distance from the origin) held constant as the pen direction rotated through a full 360 degrees. Acceleration in FIG. 3C would also be a perfect circle, with the radius being the magnitude of acceleration and the angle perpendicular to the pen velocity vector. Of course, even healthy patients like this one cannot execute a complex stroke like a circle with such perfection. Note that in FIGS. 3B and 3D, the velocity ramps up quickly to a relatively constant magnitude as the pen circles around the clockface once. The angle of pen velocity in FIG. 3B also circles around once through 360 degrees as the pen makes the full circuit around the clockface. The magnitude of velocity is a bit uneven over time, and the stroke ends abruptly without velocity returning to zero—this subject lifted the pen 155 off the paper before slowing down. Hand motion involves many subtle movements, and so despite the smoothness of the clockface outline, velocity is not as smooth as one might have expected. The second order difference example (as an approximate measure of acceleration; FIG. 3C) is even more ragged, though it does show acceleration rotating through all 360 degrees in a somewhat circular manner.

The pen speed in FIG. 3D shows the magnitude of the first order difference in mm/sec as a function of sample number. The sample rate of the pen is fixed (in this example it is 75 samples per second), so drawing time may be estimated by dividing the sample number by the sampling rate. Note that in this example it appears that the user managed to keep the pen moving at a reasonably constant speed through the entire circle.

Figure 4:
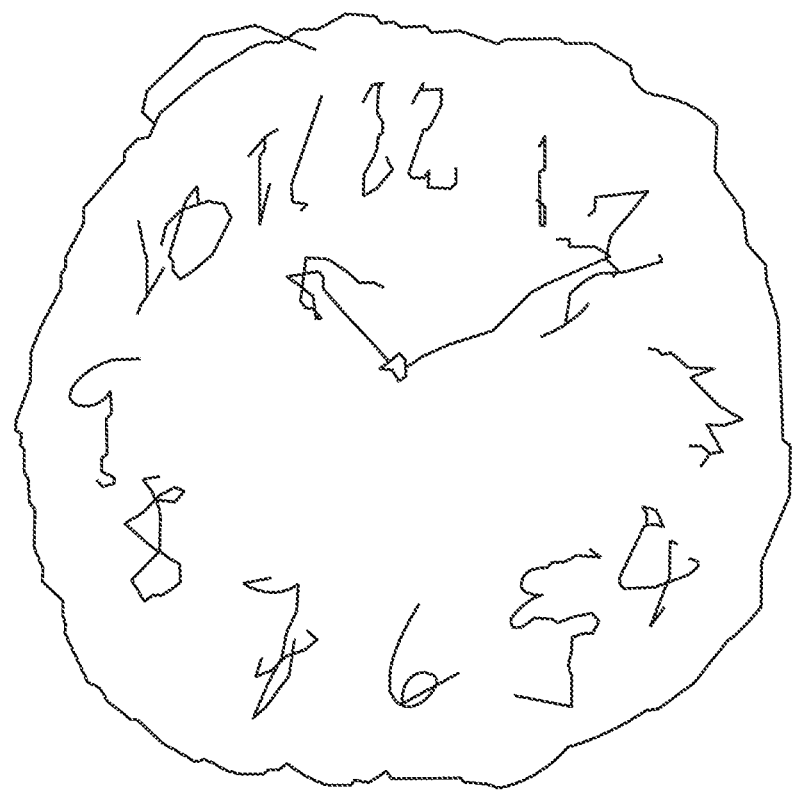
FIG. 4 depicts an example clockface composed by a patient exhibiting Essential Tremor.
Figure 5A:
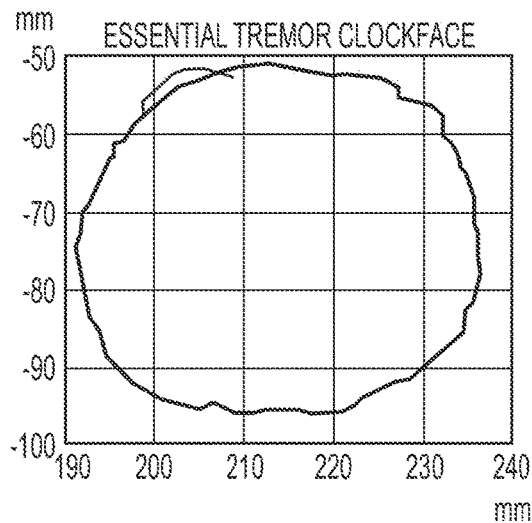
FIGS. 5A-5D depict example metrics corresponding to the drawing of a clockface by a patient exhibiting Essential Tremor.

Even with these rough measures of velocity and acceleration, the pictures look quite different for a subject with Essential Tremor, such as the clock drawing 400 example presented in FIG. 4. FIG. 5A shows, as an example, just the clockface outline plus the first and second order vector differences in FIGS. 5B and 5C, respectively, and the magnitude of the first order difference as a function of sample in FIG. 5D.

Figure 5B:
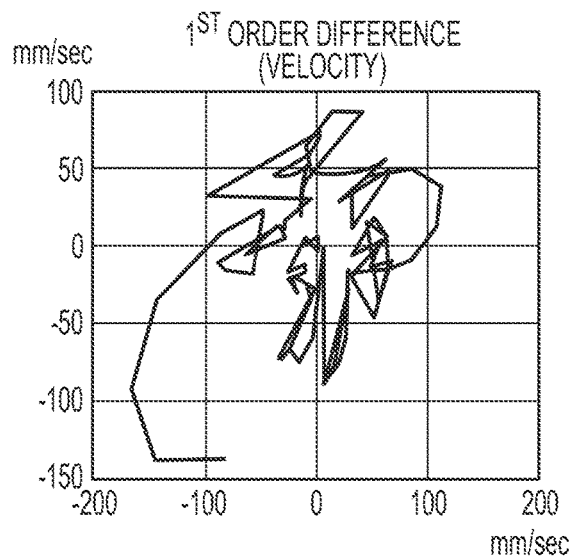
Figure 5C:
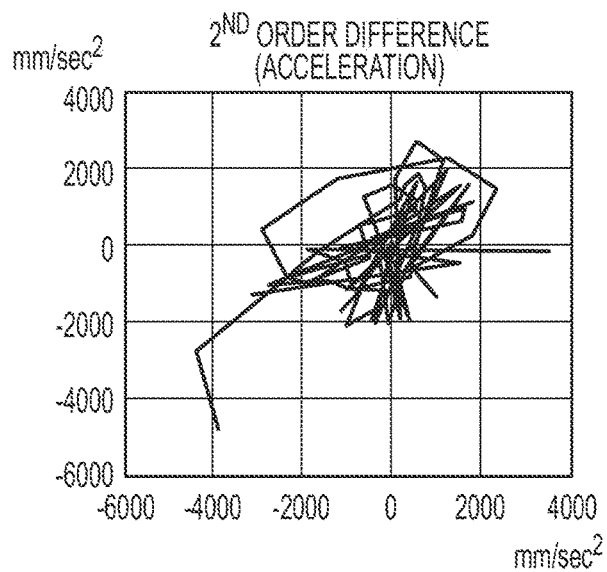
Figure 5D:
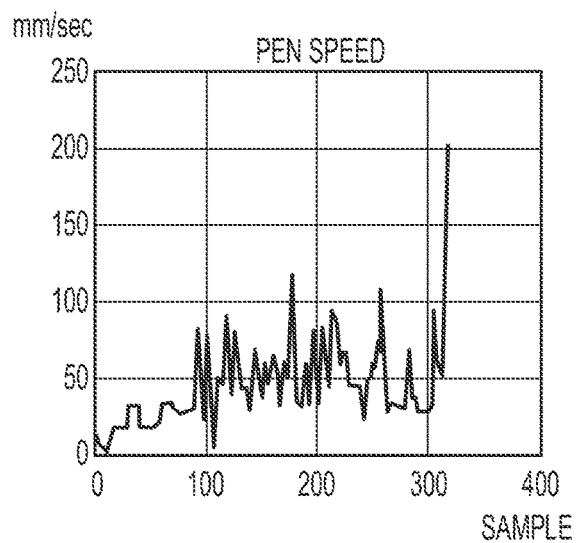

Note that the average pen speed in FIG. 3D for the healthy patient is around 80 mm/sec, but the average pen speed in FIG. 5D for the impaired patient is closer to 50 mm/sec. This user is drawing slowly, probably in order to better control their hand motion. The fluctuation in pen speed in the impaired FIG. 5D is higher than the fluctuation in pen speed in the healthy FIG. 3D. The directional velocity vector graph in FIG. 5B shows rapid oscillation in velocity, instead of the circle we would have expected, and the acceleration vector in FIG. 5C is 2-4 times higher in this impaired drawing than in the healthy drawing FIG. 3C.

Figure 6:
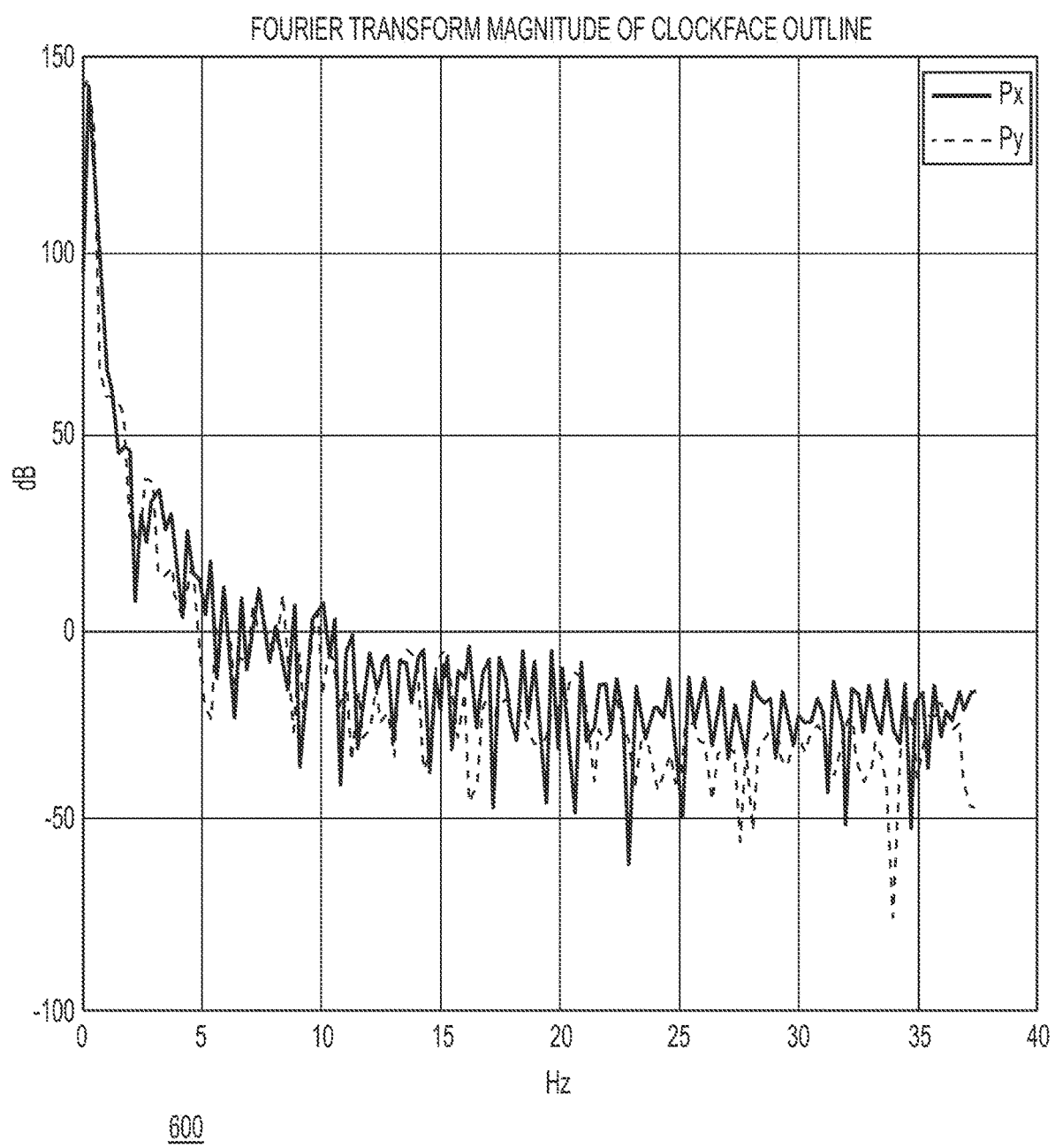
FIG. 6 depicts an example graph of a Fourier transform magnitude squared of the X and Y coordinates of a clockface drawn by a healthy patient.
Figure 7:
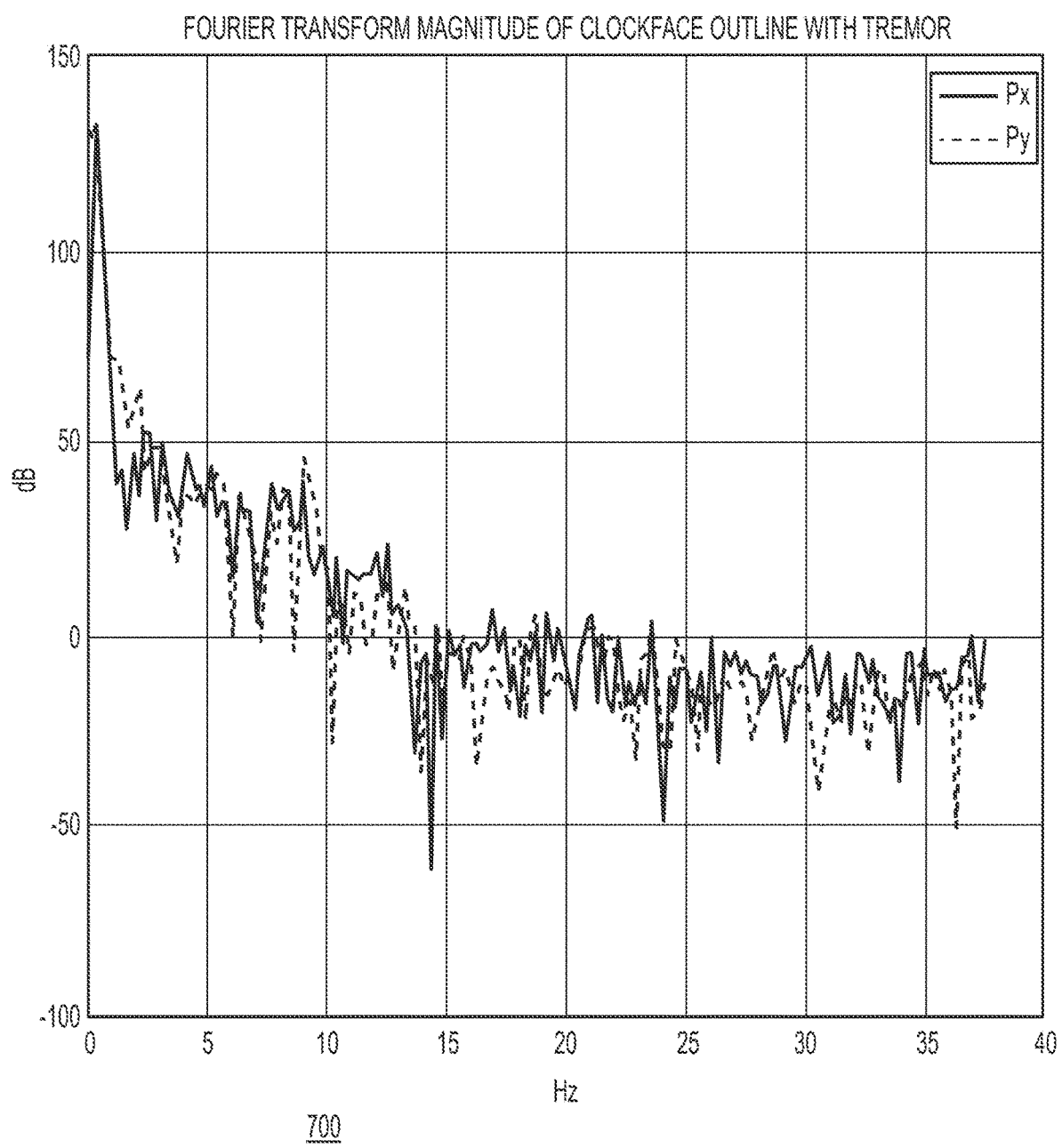
FIG. 7 depicts an example graph of a Fourier Transform magnitude squared of the X and Y coordinates of a clockface drawn by a patient exhibiting Essential Tremor.

Insight into the signal processing required to enhance the differences between healthy and tremor drawing may be gained by examining the frequency content of the drawings. FIG. 6 and FIG. 7 show example graphs 600 and 700, respectively, of the Fourier Transform magnitude squared of the X and Y coordinates of the mean-removed clockface circles from the healthy subject and from the subject with Essential Tremor. Each graph contains two plots corresponding to the Fourier Transform of the X and the Y position coordinates. There is a strong low frequency component corresponding to the gross circular motion in all the spectra, but the subject with tremor has extra energy visible in the 4-8 Hz range. There is a small amount of energy boost in the tremor subject from 9-12 Hz approximate range, but above about 13 Hz there is little apparent structural difference between the spectra of the healthy and the impaired drawings. This frequency structure is consistent with academic research suggesting that the expected frequency band of tremor should be around 4-6 Hz.

In the next two sections of this disclosure (entitled "Data Acquisition and Pre-Processing" and "Tremor Quantification Features"), algorithms are presented that quantitatively correlate with the amount of tremor without being misled by the typical unevenness of voluntary movements by healthy individuals. One technique is to measure the deviation of the drawing from the intended shape, velocity and acceleration, focusing on the tremor frequency band of 4-8 Hz while suppressing lower frequencies, which may be the result of voluntary motion, and/or suppressing irrelevant data in the upper frequencies from the pen 155.

Data Acquisition and Pre-Processing

Figure 8:
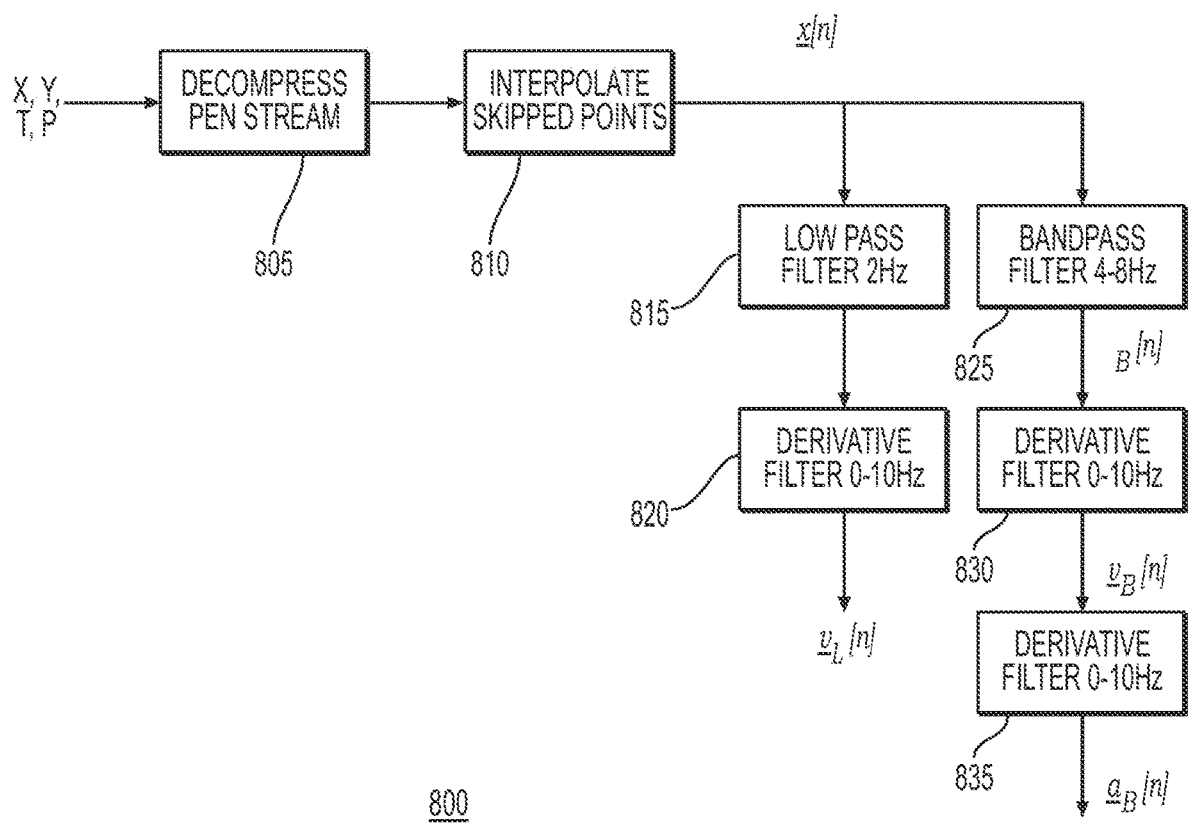
FIG. 8 depicts an example block diagram of signal processing in accordance with techniques presented herein.
Figure 9:
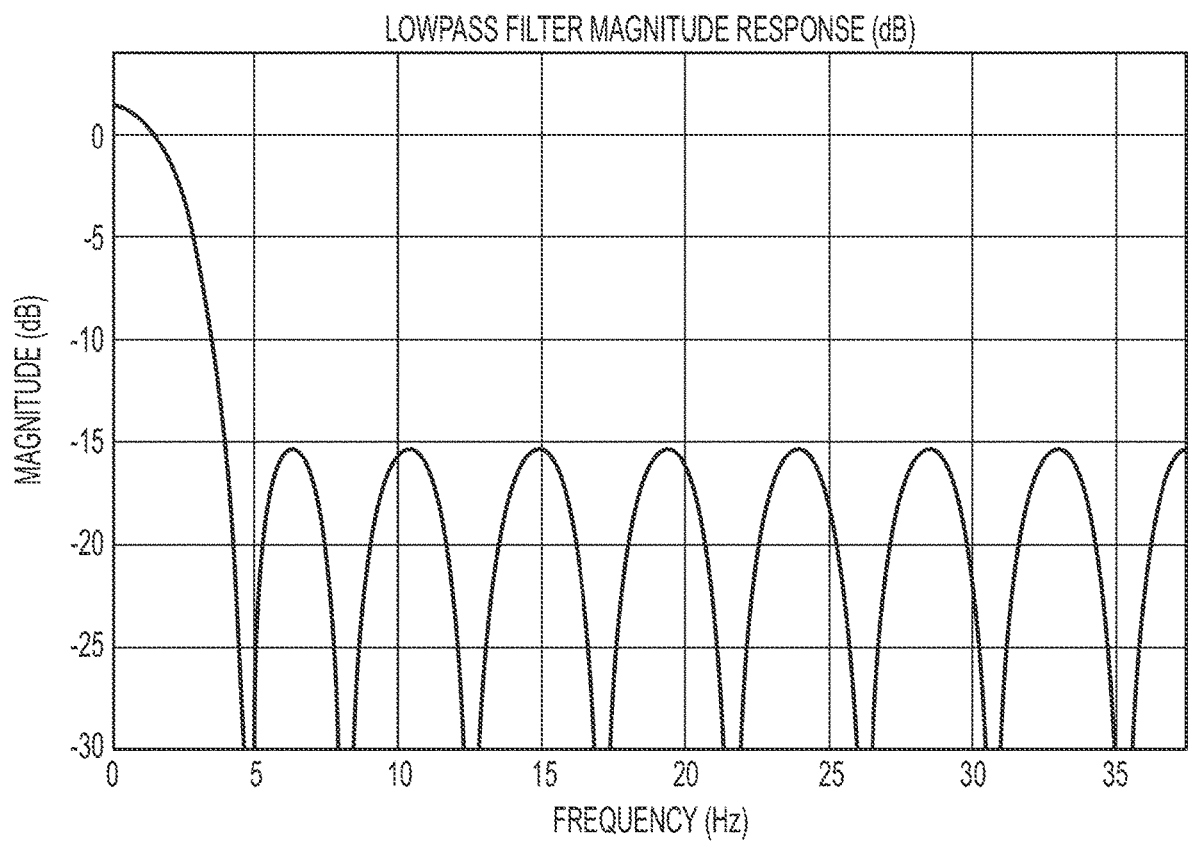
FIG. 9 depicts an example low-pass filter design in accordance with techniques presented herein.
Figure 10:
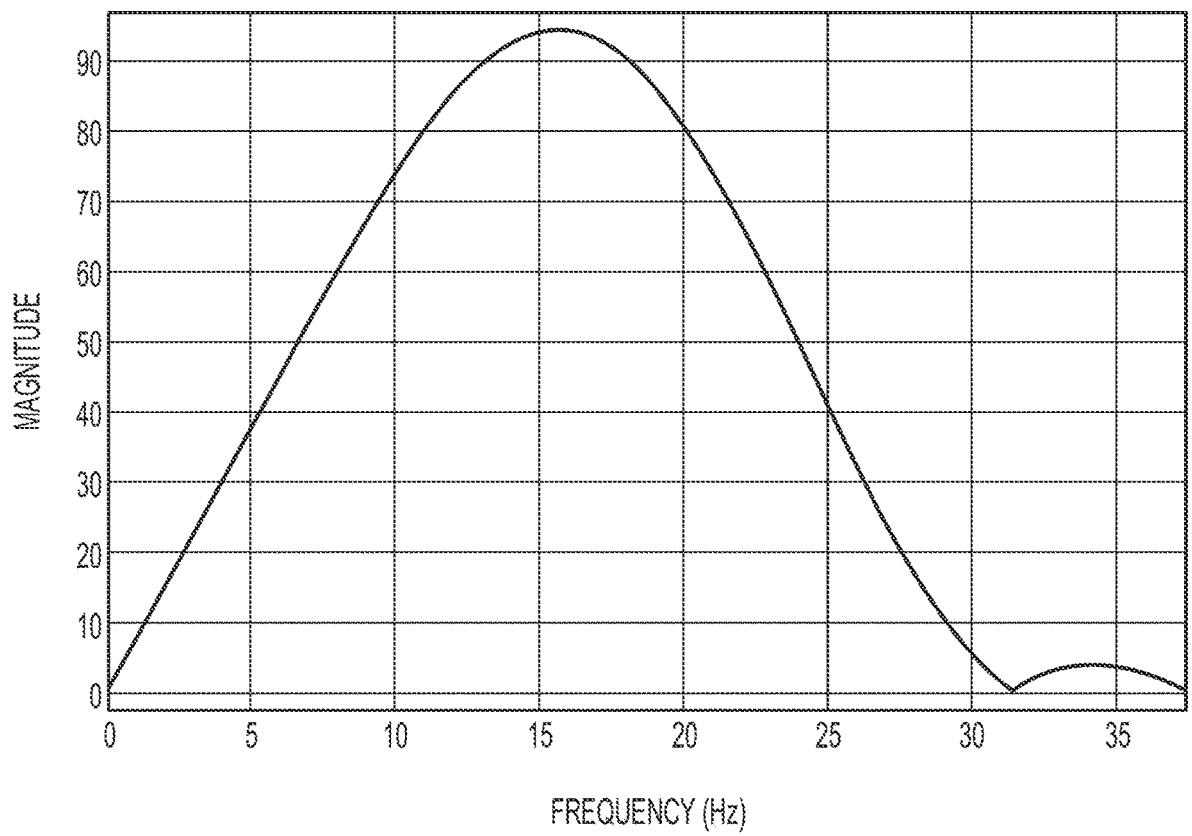
FIG. 10 depicts an example differentiator filter design in accordance with techniques presented herein.

FIG. 8 shows an example block diagram 800 of the signal processing that may be performed in accordance with techniques presented herein. First, the stream of points and strokes from the digital pen 155 may be decompressed at step 805. This data may include position data (X, Y), time data (T), pressure data (P), Tilt and Rotation, etc. For I/O data efficiency, the sampling rate may be non-uniform. For example, the pen 155 may skip over points that are in a straight line at constant speed at step 810, so these missing points may first be reconstructed through interpolation. An important improvement to estimating pen position and velocity is to use filtering in order to reduce the noise in the pen position estimates. An initial estimate may be determined of the intended direction and speed by low-pass filtering the position information, which may then be processed through a smoothed derivative filter in order to estimate velocity. For example, suppose the pen position was sampled at 75 Hz. The low-pass, shown at step 815, may be a symmetric, linear phase finite impulse response (FIR) filter of order 18, with 2 Hz cutoff (see FIG. 9). The derivative filter, shown at step 820, may be designed to behave like a first order difference up to approximately 10 Hz, but then drop into a stop band as it approaches the Nyquist frequency. For example, the derivative filter may be an odd-length order 8 anti-symmetric generalized linear phase finite impulse response (FIR) filter (see FIG. 10). The output of the first filter is a smoothed estimate of pen position as a function of time, and the second filter gives a smoothed estimate of velocity that includes the key frequency band of 4-8 Hz. Note that the input to each filter is a two-dimensional (x,y) vector function of time, and so each filter shown is really a pair of filters, one for the X component and one for the Y.

Figure 11:
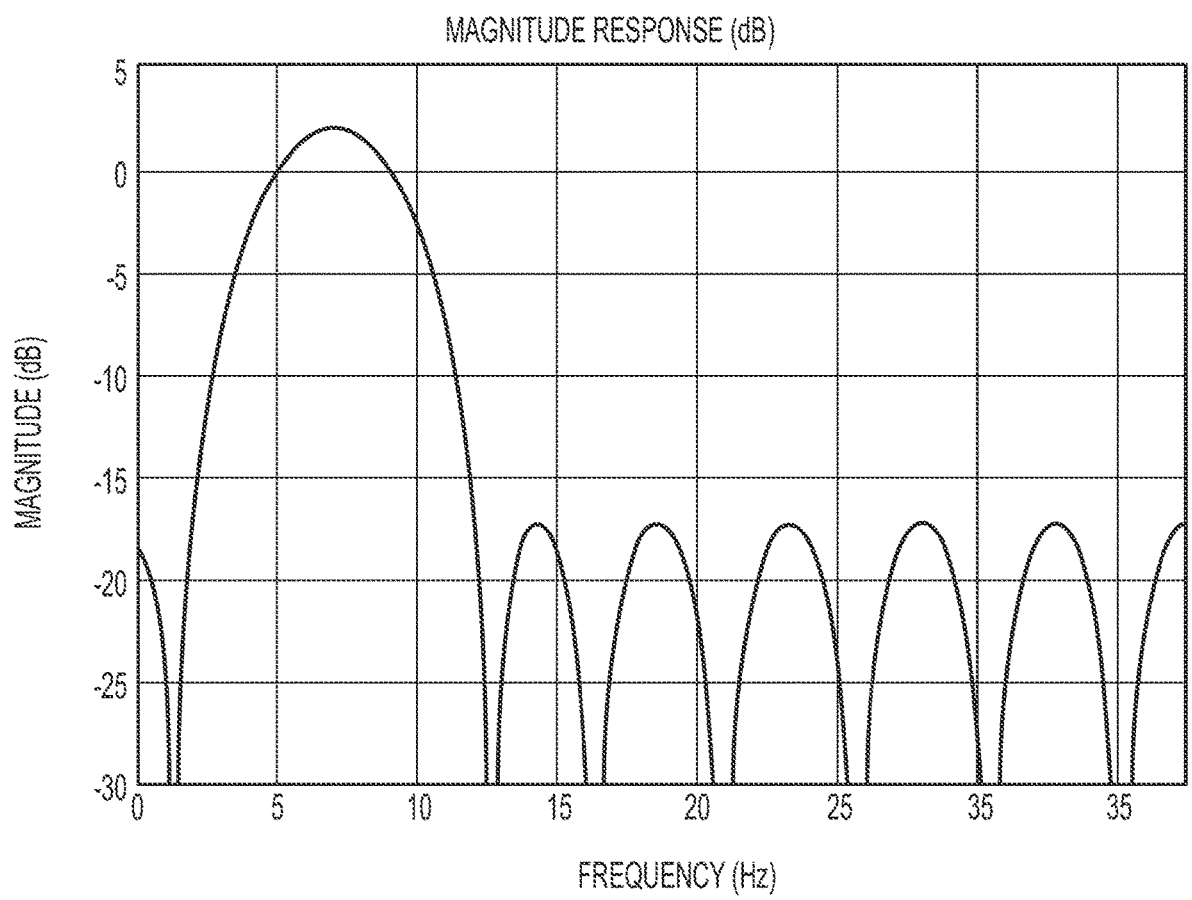
FIG. 11 depicts an example bandpass filter design in accordance with techniques presented herein.

On a separate branch, at step 825, the (x,y) pen data may be processed through a 4-8 Hz bandpass filter in order to keep only the frequencies of interest for detecting tremor. For example, this could be a bandpass FIR filter of order 18 (see FIG. 11). This may then be passed through a cascade of two smoothed derivative filters, at steps 830 and 835, to form a bandpass filtered velocity vector signal and a bandpass filtered acceleration signal. The same derivative filter design may be used as in step 820, or a different filter could be used.

The specific filters used as examples here are appropriate for a pen sample rate of 75 Hz, but may need to be modified appropriately for different pen sample rates. A variety of different low pass, bandpass and derivative filter structures could be implemented (Parks-McClellan, least squares, windowed-sinc function, infinite impulse response (IIR), etc.). In addition, the lower and upper thresholds of the frequency band of interest, 4 and 8 Hz respectively in the aforementioned embodiments, could be adjusted up or down. If the digitizing pen has relatively low noise levels, then the bandpass filter could also be replaced by a high pass filter, keeping frequencies above 4 Hz or so.

One consideration in the filter design is that the clockface outline stroke may typically be only about 70-400 samples long at 75 Hz sampling. If an FIR filter of length L (L taps) is applied to N points of data, and extrapolating the data outside the interval [0,N−1] is undesirable, then only N−L+1 samples of the output may be able to be computed. When FIR filters are cascaded, as in steps 830 and 835, the valid sample count may drop after each filtering stage. To preserve as many data samples as possible for analysis, it may be helpful to keep the filters short. On the other hand, longer filters may achieve better stopband suppression. The example filter lengths are a compromise. The bandpass acceleration signal, in our example, would be 34 samples shorter than the clockface, which means that about 20% of a clockface that took 2 seconds to draw may be lost (the sample rate is 75 Hz).

One issue is that the start and stop of each pen stroke involves different muscle movements than the middle portion, and often there are "hooklet" shapes at the start and end due to transient start/stop hand behavior. One benefit of shortening the data with each filter pass is that data corrupted by the hooklet or other start/stop motion is discarded. It also may be preferable to remove the end segments altogether before filtering to avoid contaminating the rest of the data, although this further reduces the amount of data available for analysis.

A variable length filter may instead be used that is appropriately shorter at the beginning and end of the data segment. As mentioned above, however, the ends may need to be truncated to remove the hooklets, so this alternative filtering strategy might not provide much improvement.

Figure 12A:
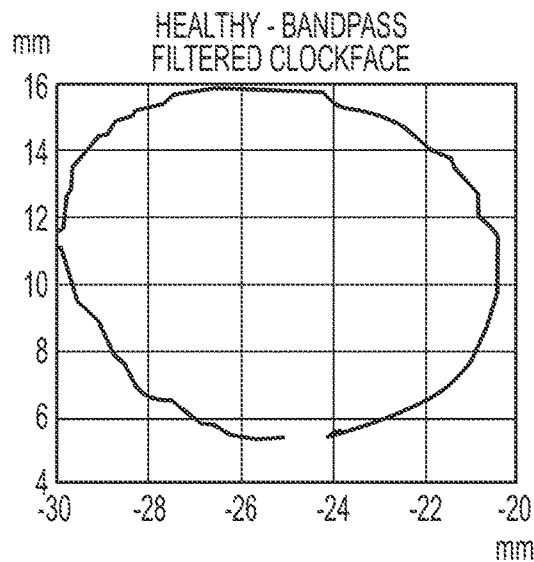
FIGS. 12A-12D depict graphs of a bandpass filtered position, velocity, acceleration, and low-pass filtered velocity of the clockface pen stroke drawn by a healthy individual, in accordance with techniques presented herein.
Figure 12B:
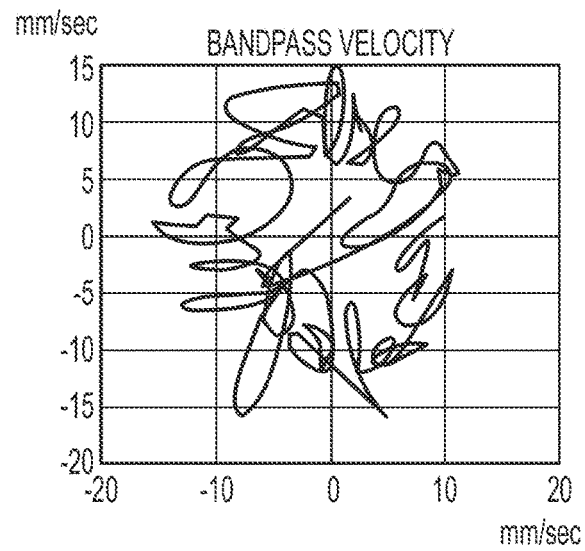
Figure 12C:
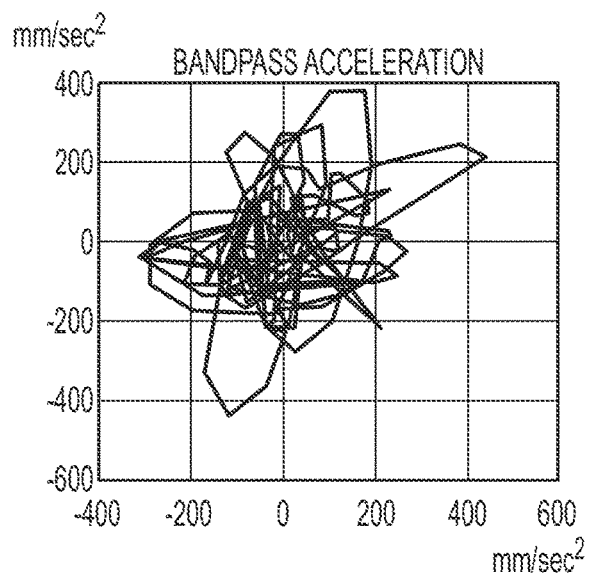
Figure 12D:
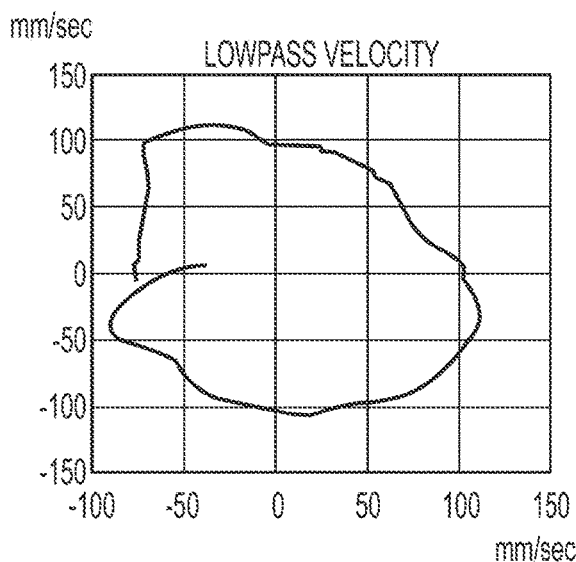

FIGS. 12A-12D show the (X,Y) components of the outputs of the filters in FIG. 8 as they evolve over time for the clockface stroke drawn by a healthy individual. FIG. 12A shows the bandpass filtered pen position signal $\underline{B}[n]$, which traces a near-circle. FIG. 12B shows the bandpass velocity signal $\underline{v}_8[n]$, and FIG. 12C shows the bandpass acceleration signal $\underline{a}_8[n]$. Both of these would be circles if the subject was drawing perfectly. Nevertheless, both of these signals are comparatively small, and are distributed somewhat uniformly in direction. FIG. 12D shows the lowpass filtered velocity $\underline{v}_L[n]$, which we would expect to be a circle if perfectly drawn, and which is recognizably close to that.

Figure 13A:
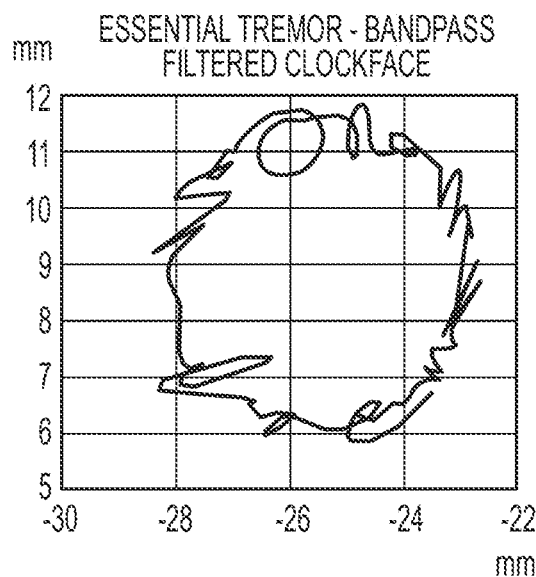
FIGS. 13A-13D depict graphs of bandpass filtered position, velocity, acceleration, and low-pass filtered velocity of the clockface pen stroke drawn by a patient with Essential Tremor, in accordance with techniques presented herein.
Figure 13B:
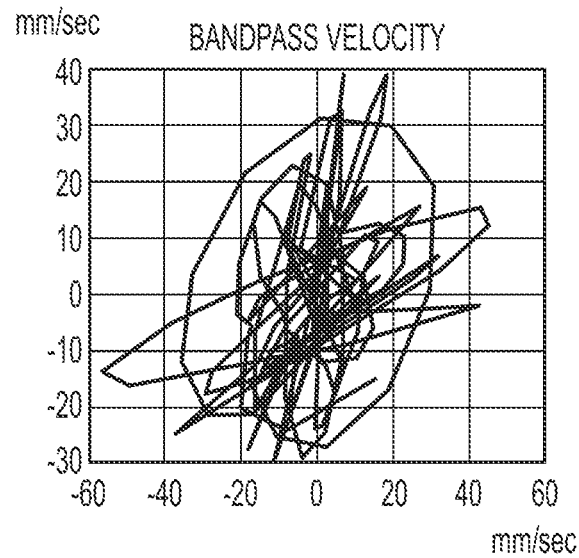
Figure 13C:
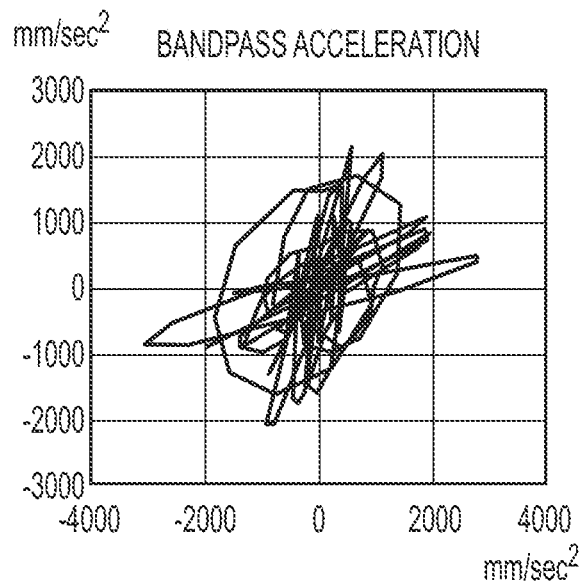
Figure 13D:
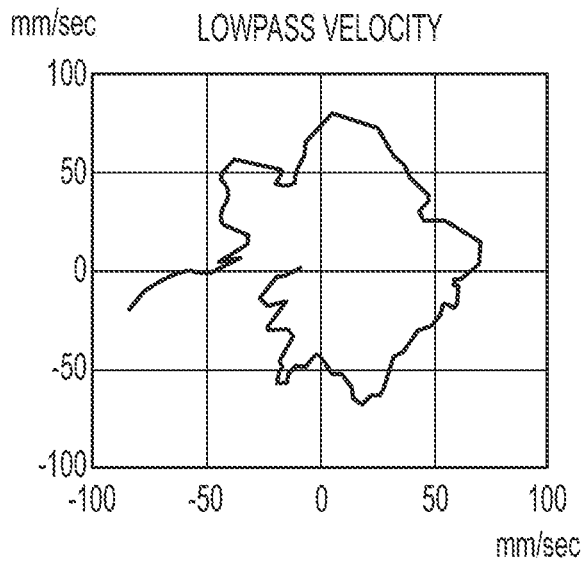

FIGS. 13A-13D show the same filtered signals for a subject with Essential Tremor. The differences between these two sets of graphs are quite clear. Low-pass velocity for the healthy subject, in FIG. 12D, is somewhat smooth, but the tremor subject in FIG. 13D, has somewhat more ragged low-pass velocity. On average, this tremor subject's low-pass velocity is about half that of the healthy subject's velocity. Bandpass velocity for the tremor subject, in FIG. 13B, is double that of the healthy subject, from FIG. 12B, and bandpass acceleration for the tremor subject (FIG. 13C) may be up to five times larger or more than that of the healthy subject (FIG. 12C). The relative sizes of these signals may be different for different patients.

Figure 14A:
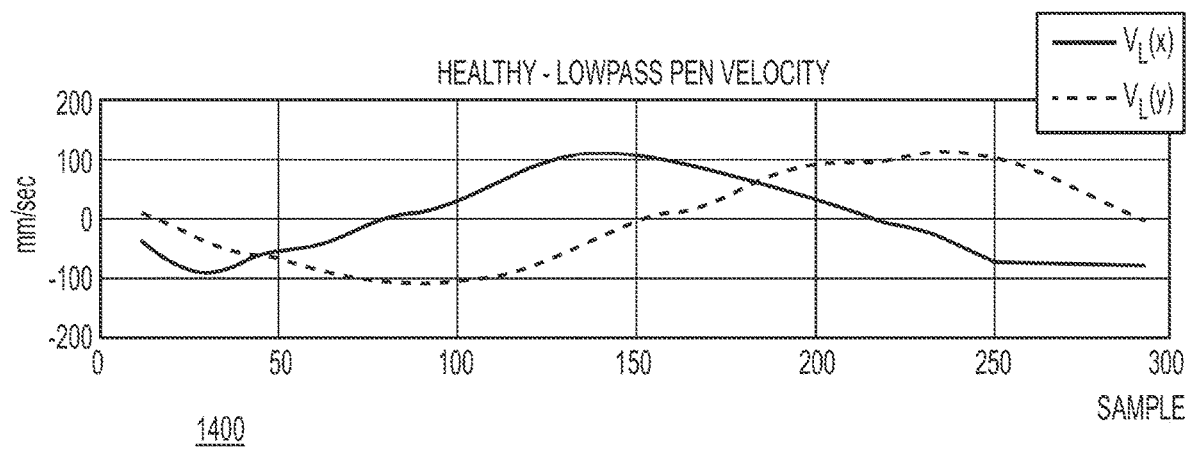
FIGS. 14A-14C depict low-pass filtered velocity, bandpass filtered velocity, and bandpass filtered acceleration, respectively, in accordance with techniques presented herein.
Figure 14B:
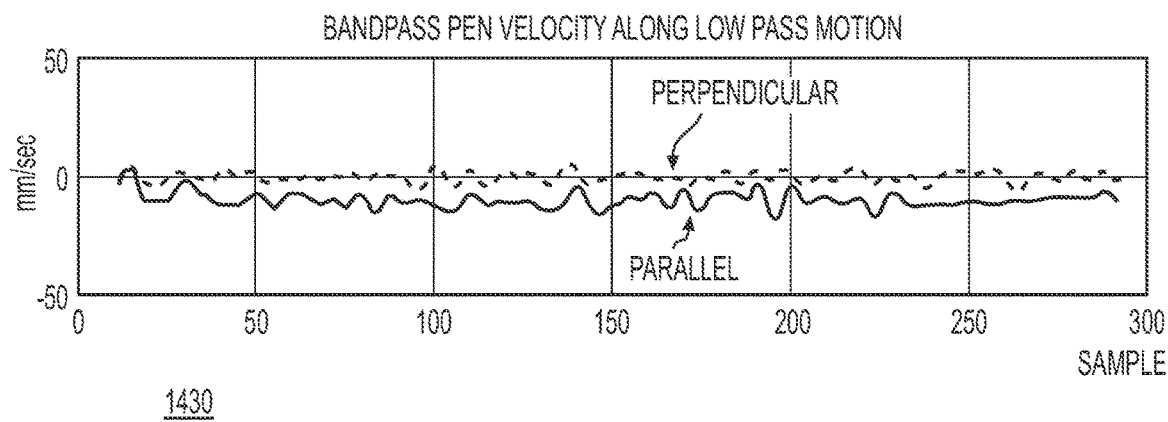
Figure 14C:
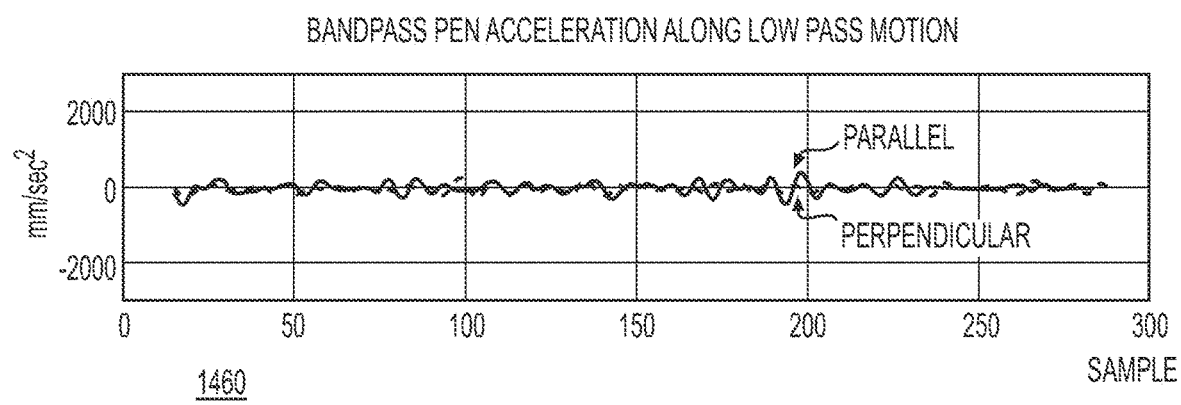

The low-pass filtered velocity may be viewed as reflecting the intended pen direction. It therefore may be useful to compute the projections of the bandpass velocity both parallel and perpendicular to the low-pass velocity, as shown in FIGS. 14A-14C. One purpose of separating out the velocity and acceleration into directions parallel to and perpendicular to the smoothed velocity curve is that tremor that is visible in the drawing to a human observer corresponds to velocity and acceleration fluctuations perpendicular to the smoothed velocity direction. Such perpendicular fluctuations result in a wavy drawn line oscillating from side to side along the stroke direction. Fluctuations in velocity and acceleration parallel to smoothed velocity are different in that they may cause the pen 155 to speed up and slow down in the general direction of travel, but they might not leave as visible a mark on the written page.

To formalize the different signals considered, it may be helpful to start by defining some notation. Let $\underline{x}[n]=(x[n],y[n])'$ be the column vector of interpolated pen positions for $n=0, \ldots, N-1$. Because the filters may be odd-length and either symmetric (low-pass, bandpass) or anti-symmetric (derivative), it may be convenient to center all the filters at the origin. Let $h_L[n]$ be the impulse response of the low-pass filter with non-zero taps$[-N_L,N_L]$, let $h_B[n]$ be the impulse response of the band-pass filter with taps$[-N_B,N_B]$, and let $h_D[n]$ be the impulse response of the derivative filter with taps $[-N_D,N_D]$. It may be convenient, though not necessary, to have the low-pass and bandpass filter lengths be the same, $N_L=N_B$. Then the smoothed, low-pass filtered position may be:

$$\underline{x}_L[n] = \sum_{k=-N_L}^{N_L} h_L[k]\underline{x}[n-k] \text{ for } n = N_L, \ldots, N-1-N_L$$

The smoothed velocity estimates may be:

$$\underline{v}_L[n] = \sum_{k=-N_D}^{N_D} h_D[k]\underline{x}_L[n-k] \text{ for } n = N_D+N_L, \ldots, N-1-N_D-N_L$$

Similarly, the bandpass filtered velocities $\underline{v}_B[n]=(v_{Bx}[n],v_{By}[n])$ and accelerations $\underline{a}_B[n]=(a_{Bx}[n],a_{By}[n])$ may be derived as follows:

$$\underline{x}_B[n] = \sum_{k=-N_B}^{N_B} h_B[k]\underline{x}[n-k] \text{ for } n = N_B, \ldots, N-1-N_B$$

$$\underline{v}_B[n] = \sum_{k=-N_D}^{N_D} h_D[k]\underline{x}_B[n-k] \text{ for } n = N_D+N_B, \ldots, N-1-N_D-N_B$$

$$\underline{a}_B[n] = \sum_{k=-N_D}^{N_D} h_D[k]\underline{v}_B[n-k] \text{ for } n = 2N_D+N_B, \ldots, N-1-2N_D-N_B$$

The velocity in the direction of pen motion may be calculated by taking the inner product between the bandpass velocity with the direction of the low-pass filtered velocity. This can also be viewed as a projection operation, and it results in the signal $v_\square[n]$. The velocity perpendicular to pen motion may be calculated by taking the cross-product between the bandpass velocity with the direction of the low-pass filtered velocity. This gives signal $v_\perp[n]$.

$$v_\square[n] = \frac{1}{\|\underline{v}_L[n]\|}(V_{Lx}[n]v_{Bx}[n] + v_{Ly}[n]v_{By}[n]) \text{ for }$$

$$n = N_D+N_B, \ldots, N-1-N_D-N_B$$

$$v_\perp[n] = \frac{1}{\|\underline{v}_L[n]\|}(v_{Lx}[n]v_{By}[n] - v_{Ly}[n]v_{Bx}[n])$$

Similarly, to compute the acceleration in the direction of pen motion, take the inner product of the bandpass acceleration with the direction of the low-pass filtered velocity, giving $a_\square[n]$. To compute the acceleration perpendicular to pen motion, take the cross-product between the bandpass acceleration with the direction of the low-pass filtered velocity, giving $a_\perp[n]$.

$$a_\square[n] = \frac{1}{\|\underline{v}_L[n]\|}(V_{Lx}[n]a_{Bx}[n] + v_{Ly}[n]a_{By}[n]) \text{ for }$$

$$n = 2N_D+N_B, \ldots, N-1-2N_D-N_B$$

$$a_\perp[n] = \frac{1}{\|\underline{v}_L[n]\|}(v_{Lx}[n]a_{By}[n] - v_{Ly}[n]a_{Bx}[n])$$

If the user were drawing a perfect circle at constant velocity, and we ignore the filtering for the moment, then we would expect $v_\square[n]$ to be the pen velocity, and $v_\perp[n]$ would be zero. We would expect acceleration to be perpendicular to the velocity and aligned in the radial direction when drawing a perfect circle so that $a_\square[n]$ should be zero and $a_\perp[n]=v_\square^2[n]/\text{Radius}$. Of course, even healthy subjects do not draw perfect circles.

FIGS. 14A-14C show these signals for the example healthy individual. FIG. 14A displays an example graph 1400 of a low-pass velocity, showing the X and Y components of the smoothed velocity vector. If the drawing were a perfect circle, these curves would look like cosines and sines, and the curves do in fact resemble those shapes. FIG. 14B displays an example graph 1430 showing bandpass velocity projected parallel and perpendicular to the smoothed low-pass velocity vector ($v_\square[n]$ and $v_\perp[n]$). The perpendicular velocity component is close to zero, though there is some fluctuation. FIG. 14C shows an example graph 1460 of bandpass acceleration projected parallel and perpendicular to the low-pass velocity vector. Both components are comparatively small.

Figure 15A:
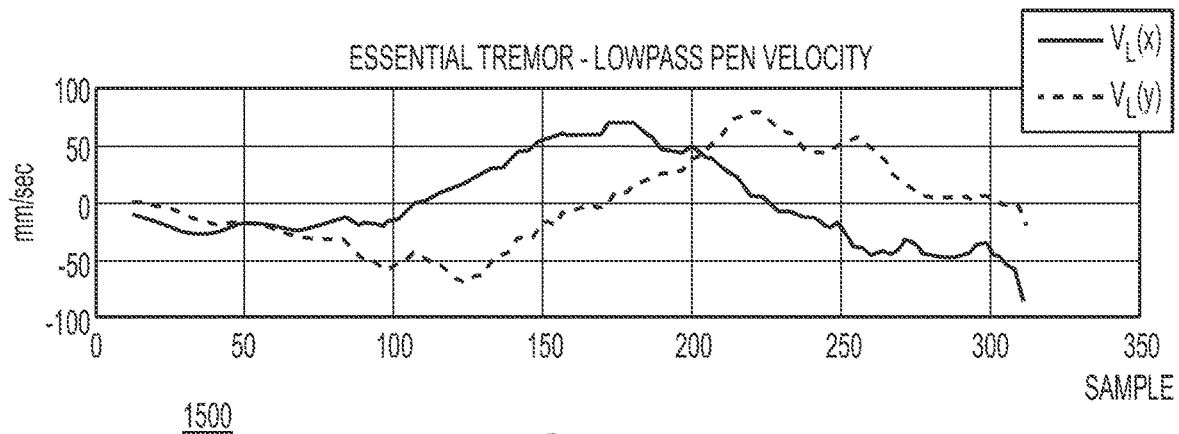
FIGS. 15A-15C depict low-pass filtered velocity, bandpass filtered velocity, and bandpass filtered acceleration associated with a patient exhibiting tremor, in accordance with techniques presented herein.
Figure 15B:
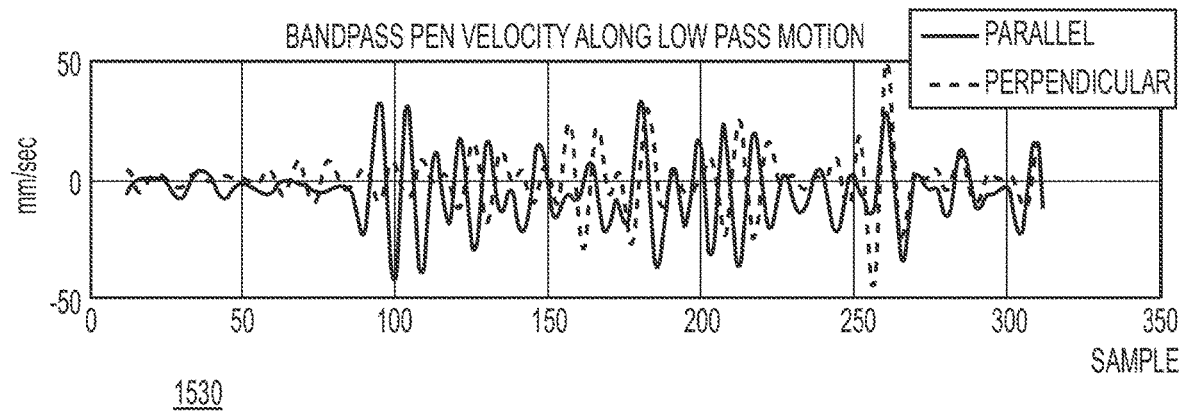
Figure 15C:
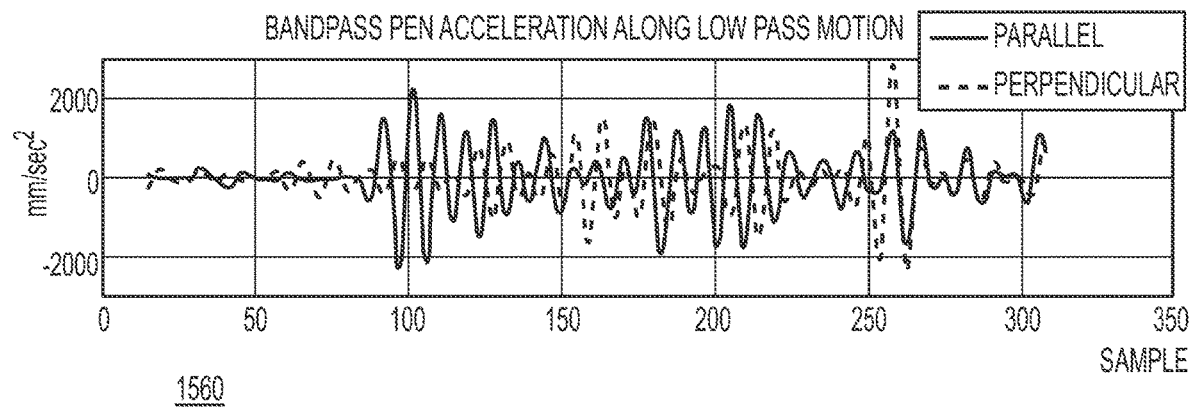

FIGS. 15A-15C depict the same signals, but for a patient exhibiting tremor. FIG. 15A displays an example graph 1500 of the low-pass filtered pen velocity of a patient with tremor. Note that it is more distorted than FIG. 14A. FIG. 15B displays an example graph 1530 of the bandpass filtered pen velocity of a patient with tremor, and FIG. 15C displays an example graph 1560 of the bandpass filtered pen acceleration of a patient with tremor. Note that, unlike the ideal case, the parallel and perpendicular components of both velocity and acceleration are of comparable magnitude, and the size of the oscillations in the acceleration in particular are much larger than the acceleration components of the healthy patient. Although there is oscillatory behavior in these signals due to the tremor, the frequency may not be fixed and the amplitude may depend on the precise position of the hand and the relative velocity direction.

Note that these tremor signals are large and measurable even though the person writing has their hand resting on the paper and may be trying hard to keep the pen steady.

Tremor Quantification Features

There are a number of ways that the strength of the bandpass velocity and acceleration signals could be used to quantify the tremor. The system could measure the total energy in one or more of the bandpass filtered and/or parallel/perpendicular signals, different energy norms could be used (sum of squares, L1 norm, and so forth), higher order derivatives could be measured, windows could apply different weights to the center vs. the ends of the stroke in a fixed or adaptive manner, and so forth. As an example, some useful features that correlate well with tremor are:

$$PnAccLogEnergy = \log\left(\frac{1}{K_A M_A}\sum_n \|\underline{a}_B[n]\|^2\right)$$

$$PnCurvLogEnergy = \log\left(\frac{1}{K_A M_A}\sum_n a_\perp^2[n]\right)$$

$$PnAccParLogEnergy = \log\left(\frac{1}{K_A M_A}\sum_n a_\square^2[n]\right)$$

$$PnSpdLogEnergy = \log\left(\frac{1}{K_V M_V}\sum_n \|\underline{v}_B[n]\|^2\right)$$

$$PnSpdPerpLogEnergy = \log\left(\frac{1}{K_V M_V}\sum_n v_\perp^2[n]\right)$$

$$PnSpdParLogEnergy = \log\left(\frac{1}{K_V M_V}\sum_n v_\square^2[n]\right)$$

Here PnAccLogEnergy is the energy (sum of squares) of the bandpass filtered acceleration magnitude, normalized by dividing by the number of terms in the sum, $M_A = N - 4N_D - 2N_B$, and further normalized by a scaling factor, $K_A$, that may compensate for drawing size, drawing time, overall speed, and so forth. The log( ) function may be used to make the distribution of feature values look more Gaussian. PnCurvLogEnergy is a similar feature that only sums the energy in the acceleration component perpendicular to pen motion. This can also be thought of as a measurement of the energy of the curvature of the stroke. PnAccParLogEnergy measures the energy in the acceleration component parallel to the pen motion. PnSpdLogEnergy is the energy (sum of squares) of the bandpass filtered velocity magnitude, normalized by dividing by the number of terms in the sum, $M_V = N - 2N_D - 2N_B$, and further normalized by a scaling factor, $K_V$, that may compensate for drawing size, drawing time, overall speed, and so forth. The log( ) function may be used to make the distribution of feature values look more Gaussian. PnSpdPerpLogEnergy is similar, but it sums the energy in the perpendicular bandpass velocity signal. PnSpdParLogEnergy is similar, but it sums the energy in the parallel bandpass velocity signal.

The normalizing factors may be important to achieving good results. For example, suppose the subject doubled the height and width of the drawing but still drew the clock in the same amount of time. All velocities and accelerations would double. On the other hand, if the diagram were drawn in the same size but in twice the time, the velocities would halve and the accelerations would drop by a quarter. In both of these examples, however, it may be desirable for the tremor feature value to remain unaltered. Compensating for these factors may be important because individuals affected by movement disorders may draw relatively small diagrams, moving the pen carefully and slowly.

One example technique is to normalize the bandpass velocity by dividing by the average velocity one would expect given the length of ink and the time required to draw the clockface.

$$\underline{\tilde{v}}_B[n] = \underline{v}_B[n]/V_{avg} \text{ where } v_{avg} = \frac{\text{Length of Ink}}{\text{Drawing Time}}$$

Doubling the size or doubling the time would then leave features depending on bandpass velocity unchanged. Similarly, bandpass acceleration may be normalized by dividing by the average acceleration:

$$\underline{\tilde{a}}_B[n] = \underline{a}_B[n]/a_{avg} \text{ where } a_{avg} = \frac{\text{Length of Ink}}{\text{Drawing Time}^2}$$

The preceding embodiments may underestimate the complexity of the normalization problem since speeding up and slowing down or drawing large or small may also change the frequency content of the tremor, which in turn may change how much energy passes through the bandpass filter and thereby change the feature. It may not be clear how the amplitude and frequency of the tremor changes when the subject tries to write faster or larger. In some embodiments, velocity and acceleration may be normalized by the same or similar factor, the square of the ratio of ink length to drawing time. For the features above, this may yield normalizing constants:

$$K_A = K_V = \left(\frac{\text{Length of Ink}}{\text{Drawing Time}}\right)^2$$

Similar strategies may use the size of the drawing, size of the bounding box, average radius, and so forth, instead of length of ink.

Each of the features described above may increase with tremor, and so may be viewed as tremor scores. Other variations of these features such as those discussed earlier can be devised that may also behave as tremor scores. In addition, multiple features may be combined in formulas or algorithms in order to build yet other tremor scores.

The digital clock test may have two separate clock drawings, the "command" where the individual draws the clock from memory, and the "copy" where the individual copies a pre-drawn clock. Tremor may be estimated using the two outline strokes separately, and scores may be combined from the two clockfaces in the two clocks. Including more pen stroke data (such as data obtained when drawing additional details of the clock, e.g. numbers and hands) may improve the ability to distinguish between presence and absence of tremor. In addition, multiple features may be combined, for example a feature using velocity may be combined with another using acceleration, in an attempt to use whatever additional information might be available. These ideas are now discussed in the context of data collected from a trial of this system.

Comparing Essential Tremor and Healthy Subjects

Figure 16A:
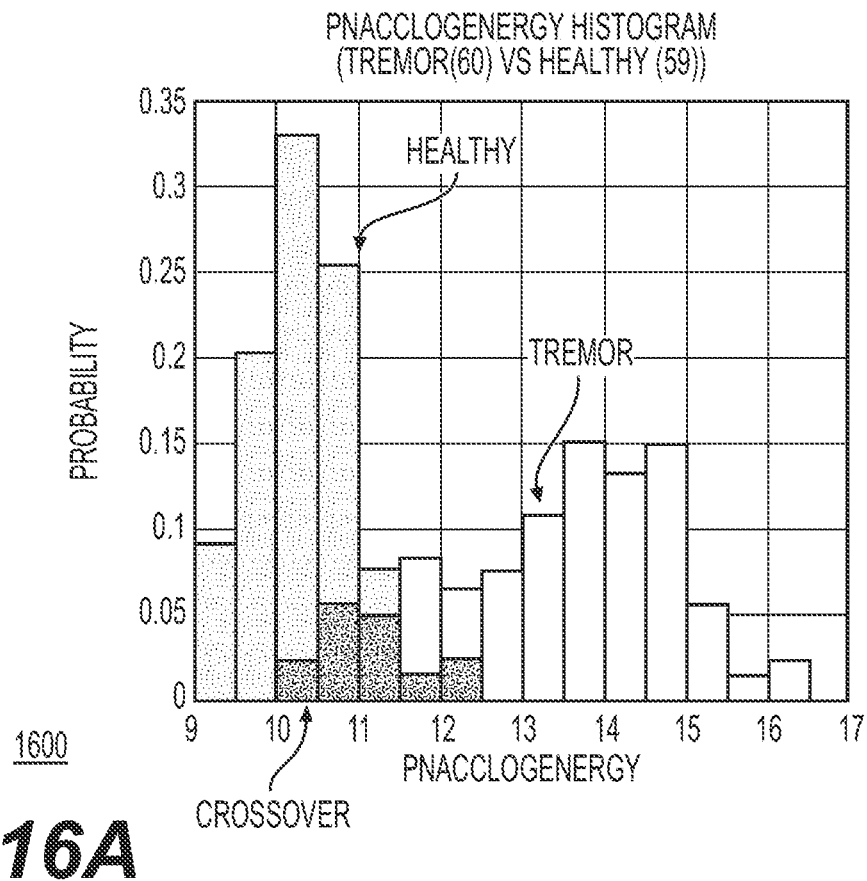
FIGS. 16A-16C depict histograms of patients with Essential Tremor and healthy population, in accordance with techniques presented herein.
Figure 16B:
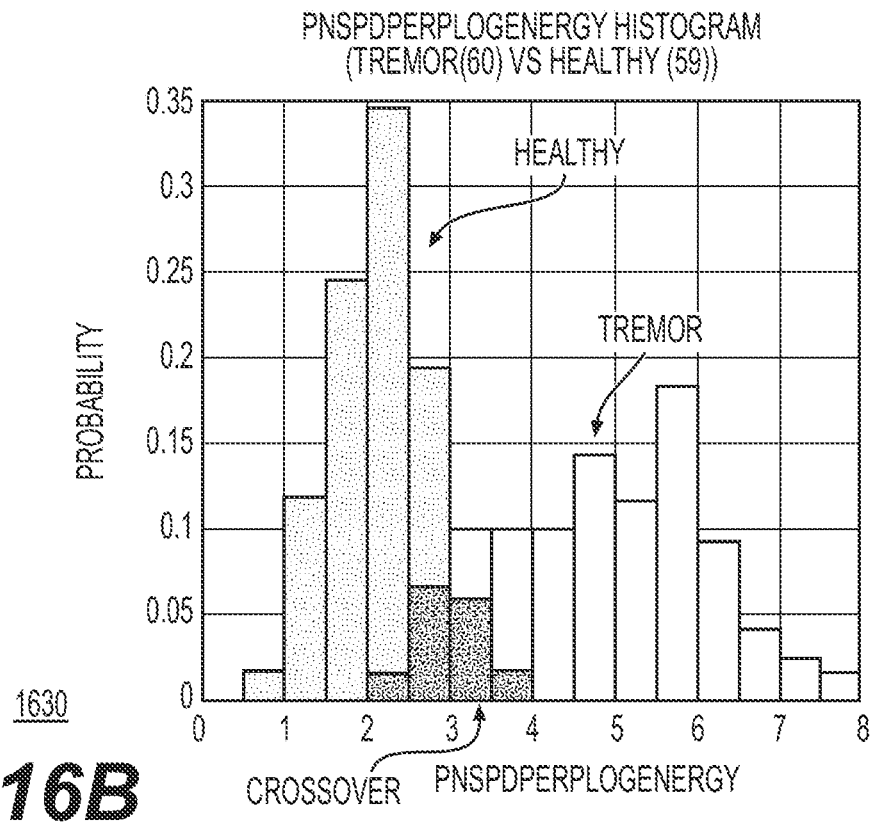
Figure 16C:
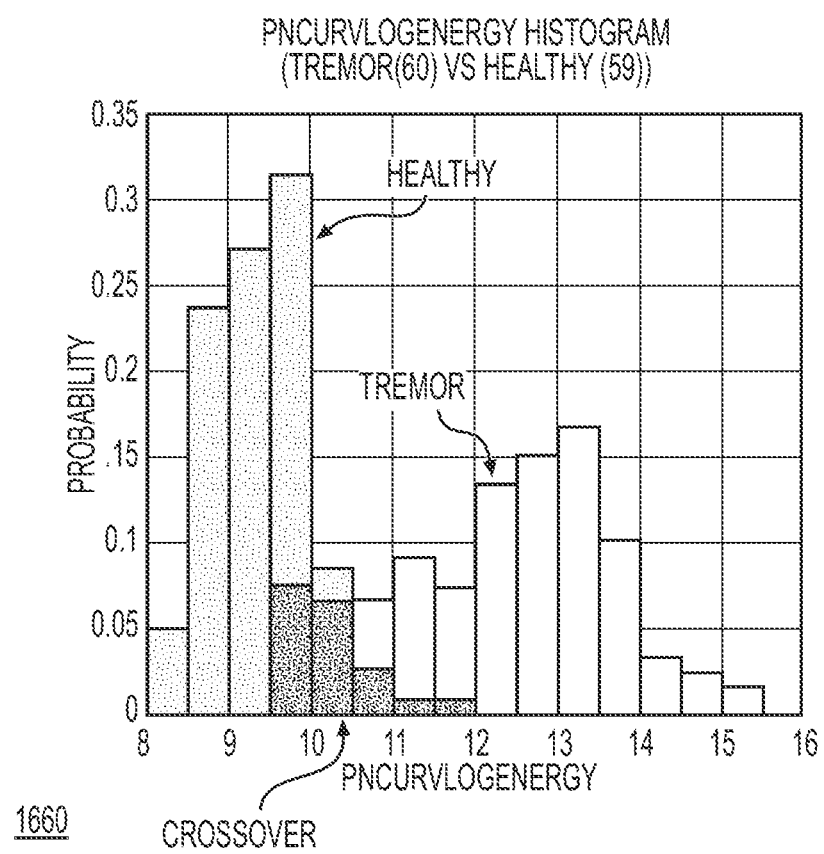

Subjects were selected who were diagnosed to have Essential Tremor (60 total, 36 males, age 65.6±11.8 years) or who were healthy controls (59 total, 14 males, age 55.1±12.5 years). They were administered Digital Clock Drawing tests, and the features on each of the command and copy clockface outlines were computed for these subjects. When the Digital Clock Test is used to screen for cognitive impairments, the Command and Copy clocks may have quite different characteristics, but they may be equally susceptible to tremor and may be treated equally. As shown in FIGS. 16A-16C, histograms were computed of each feature for the healthy and Essential Tremor populations, and ROC curves were computed by considering all possible thresholds. Effective measures for this data set included PnAccLogEnergy, the energy in the bandpass acceleration, as shown in graph 1600 in FIG. 16A, PnSpdPerpLogEnergy, the energy in the bandpass velocity perpendicular to the low pass filtered velocity, as shown in graph 1630 in FIG. 16B, and PnCurvLogEnergy, the energy in the component of bandpass acceleration perpendicular to the smoothed velocity (curvature), as shown in FIG. 16C.

In this test, these histograms were normalized by dividing by the number of clockfaces so that the height of each bar represented a frequency of occurrence. In general, for all three scoring metrics, subjects with tremor have scores that were usually larger than scores of healthy subjects. In all three cases, there is some overlap in scores between the tails of the tremor and healthy populations (denoted as "crossover" in FIGS. 16A-16C.) In general, though, these three metrics had comparable performance at separating the Essential Tremor and healthy populations.

Figure 17:
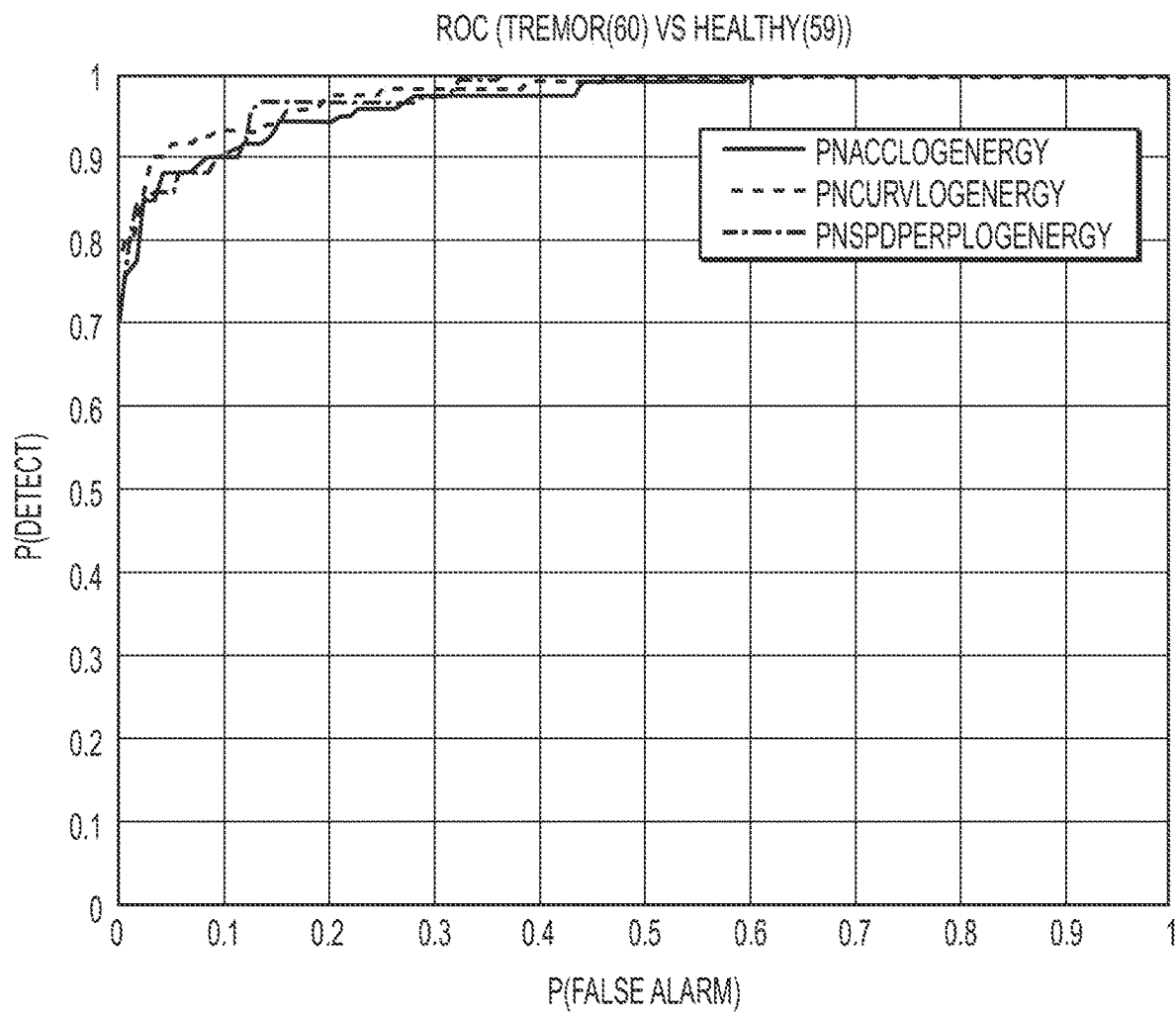
FIG. 17 depicts an example graph of receiver operating characteristic (ROC) curves for three tremor metrics in healthy vs. Essential Tremor patients.

FIG. 17 discloses an example graph 1700 of the Receiver Operating Characteristic (ROC) curves for these metrics. To generate a ROC, a feature like one discussed above is chosen and compared with a threshold. If the score is above that threshold the subject is assigned the "tremor" label, and if below then the subject is assigned the "healthy" label. The probability of false alarm (PF) is the fraction of subjects who have been diagnosed by medical professionals as healthy, but whose feature scores are above threshold. The probability of detect (PD) is the fraction of subjects who have been diagnosed by medical professionals as having tremor, and for whom the feature score is above threshold. The ROC curve may be built by calculating PF and PD for all possible thresholds and plotting these two statistics in a 2D graph. At one extreme with the threshold set to $-\infty$ no patients are diagnosed as having tremor so PF=0 and PD=0. At the other extreme with the threshold set to $+\infty$ all patients are diagnosed as having tremor, so PF=1 and PD=1. A perfect test would have a threshold such that PF=0 and PD=1. Note that the ROC curve in FIG. 17 shows that performance is not perfect, but it is possible to set the threshold so that PF:10% while PD≥90%.

A metric called Area Under the Curve (AUC) measures the area underneath the ROC curve. A perfect test would have AUC=1.0, while a test that had no discrimination ability at all would have AUC=0.5. Area Under the Curve (AUC) values from the data set presented earlier are in Table 1. The first column gives the AUC if each clockface circle is considered independently. The second column shows the AUC if the scores for the two clockfaces from each subject are averaged. These AUC scores are all close to 1.0.

TABLE 1

AUC for different metrics, treating the
two drawing separately or combined

| Metric | Command and Copy separately | Command + Copy combined |
|---|---|---|
| PnAccLogEnergy | 0.970 | 0.977 |
| PnCurvLogEnergy | 0.977 | 0.987 |
| PnSpdPerpLogEnergy | 0.980 | 0.987 |

To describe what the feature values imply about visible tremor in the drawings, the healthy and Essential Tremor subjects whose graphs were shown in FIGS. 3 and 5 had the following feature values:

TABLE 2

Values for Healthy and Essential Tremor
Subjects in the Earlier Examples

| Subject | PnAccLogEnergy | PnCurvLogEnergy | PnSpdPerpLogEnergy |
|---|---|---|---|
| Healthy Subject (FIG. 3A-3D) | 9.4 | 8.4 | 1.09 |
| Essential Tremor Subject (FIG. 5A-5D) | 13.9 | 13.0 | 5.21 |

Figure 18:
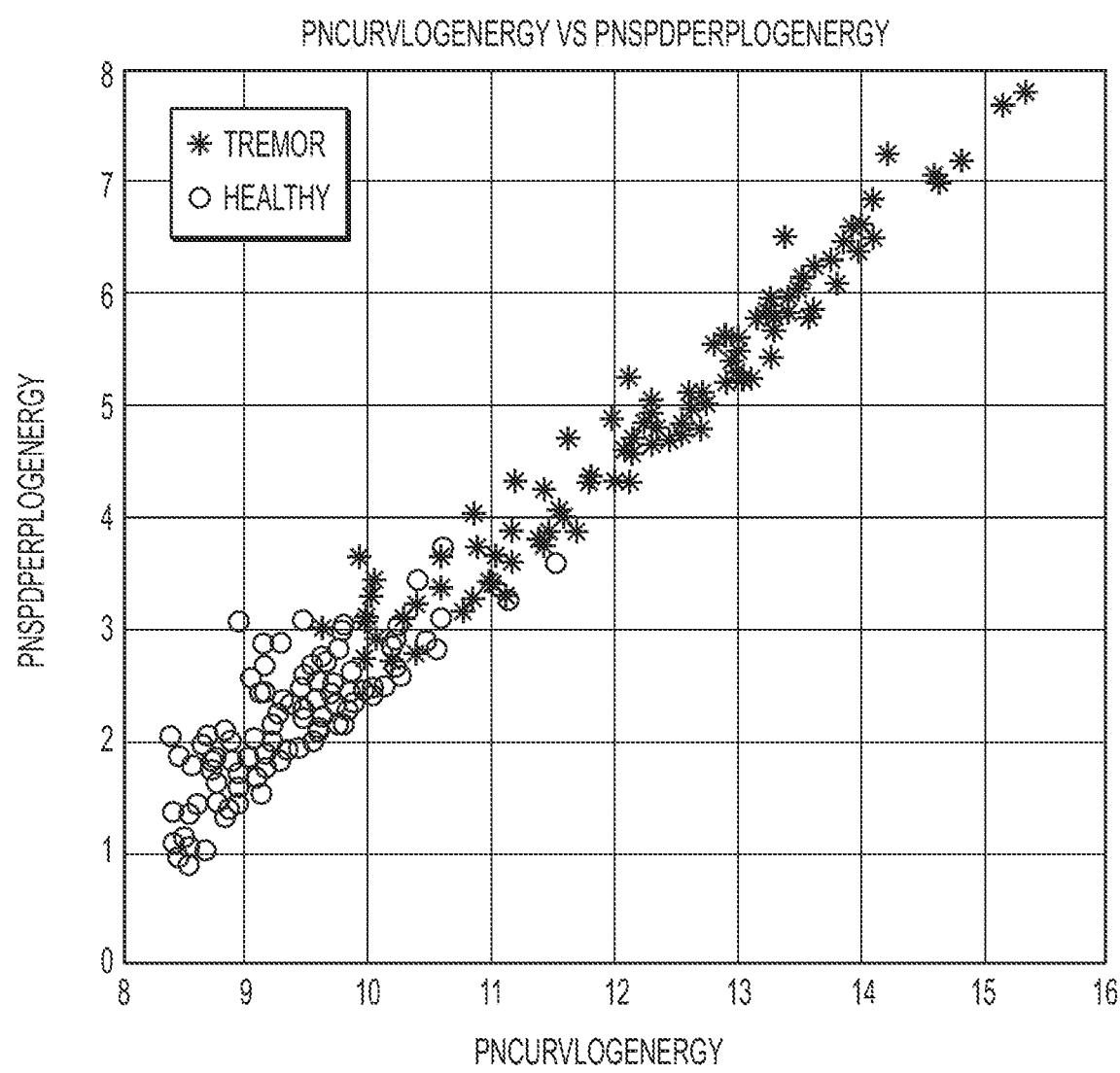
FIG. 18 depicts an example graph of PnSpdPerpLogEnergy vs. PnCurvLogEnergy in healthy and tremor-exhibiting patients, in accordance with techniques presented herein.

Other features from both drawings may be used to further improve the score. For example, on the data set disclosed above, if (PnCurvLogEnergy+PnSpedPerpLogEnergy)/2. is averaged over the two drawings and used as the score, it raises the AUC for this particular dataset to 0.99. However, in general, the gains from combining these features may be limited because they may be highly correlated. FIG. 18 discloses an example graph 1800 that plots PnCurvLogEnergy against PnSpdPerpLogEnergy for each of the drawings for the Essential Tremor and Healthy populations. Note that the values cluster tightly along a line, suggesting strong correlation between these metrics, which in turn implies that little additional information is gained by using both.

Comparing Essential Tremor Subjects with Others

Tremor may be compared with diagnoses of other neurological conditions, including Parkinson's Disease, Alzheimer's Disease, vascular dementia, and others. To do this, the patient database may be expanded to include patients with a wide variety of neurological conditions in addition to Essential Tremor. The key difficulty is that many neurological disorders, most notably Parkinson's, may have tremor as a side effect. Patients whose primary diagnosis is not Essential Tremor may therefore score high on the tremor scales discussed above, not because of a flaw in the algorithms, but because tremor is a secondary effect associated with their primary disease.

The ability of these tremor quantification metrics to pick up tremor and in distinguishing medical conditions from each other may be further improved and extended. Some examples are:

Using these tremor quantification metrics and other metrics extracted from the drawing process to distinguish the tremor associated with Essential Tremor from the tremor associated with Parkinson's disease.

Monitoring the tremor quantification metrics over time in order to track changes in Essential Tremor.

Tracking changes in tremor in subjects that undergo Deep Brain Stimulation surgery.

Mild Tremor

Figure 19:
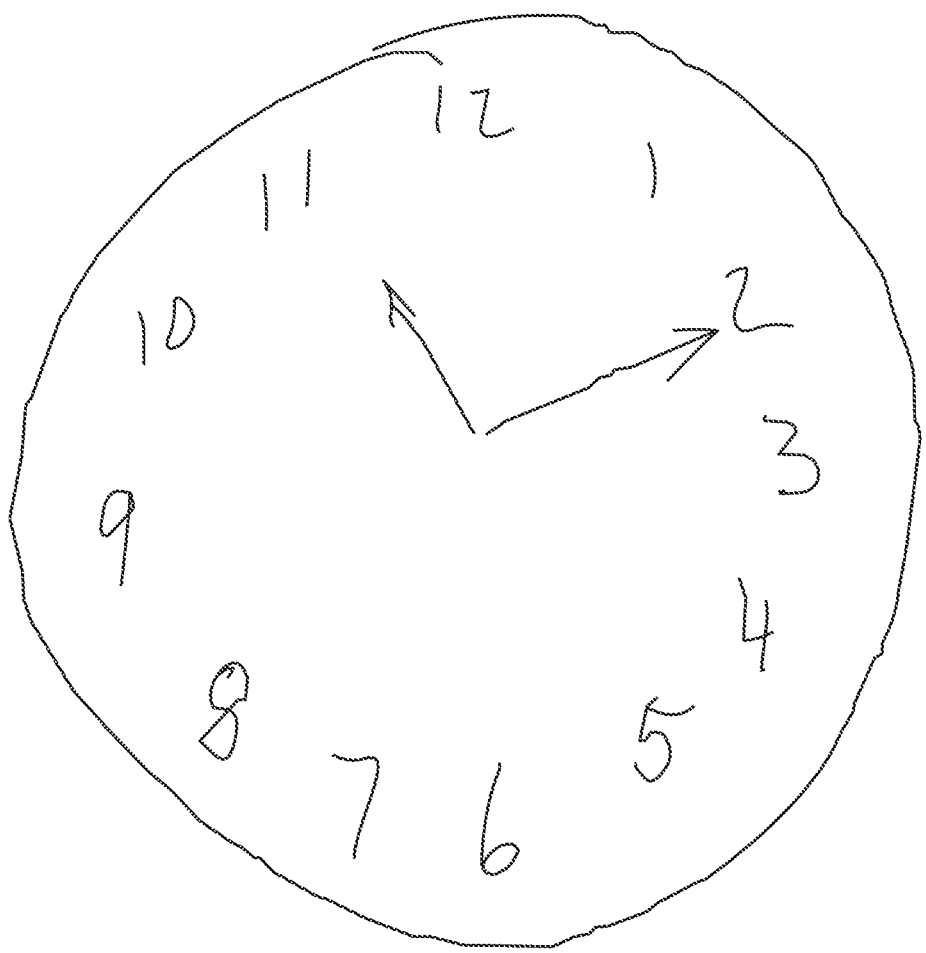
FIG. 19 depicts an example clock drawing made by a patient with Mild Tremor.
Figure 20A:
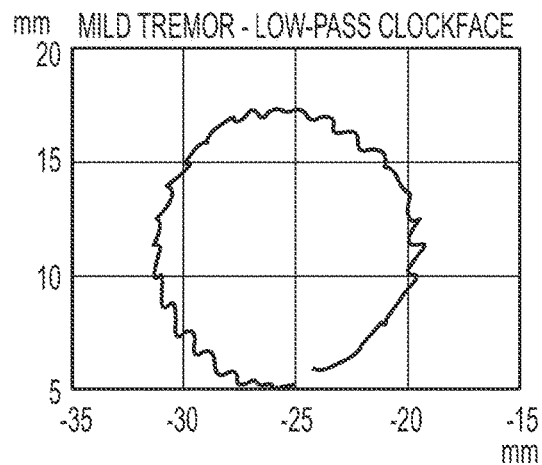
FIGS. 20A-20D depict example metrics associated with the clock drawing made by a patient with Mild Tremor, in accordance with techniques presented herein.
Figure 20B:
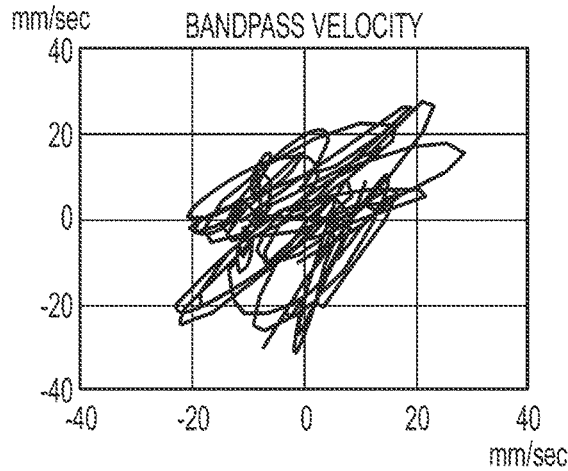
Figure 20C:
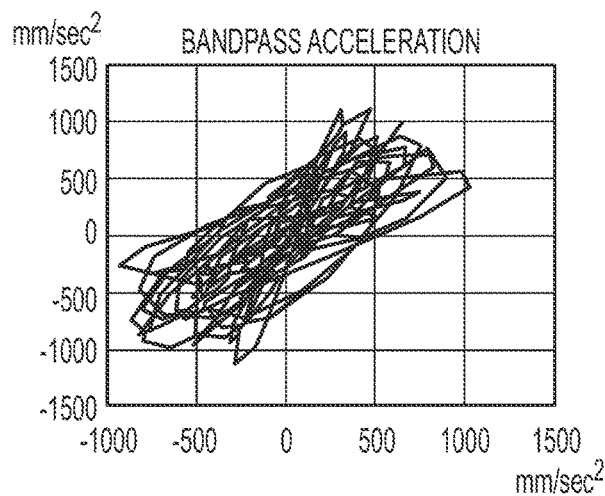
Figure 20D:
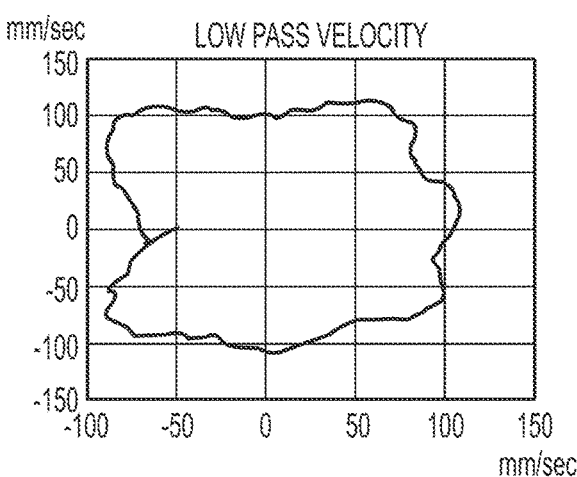
Figure 21:
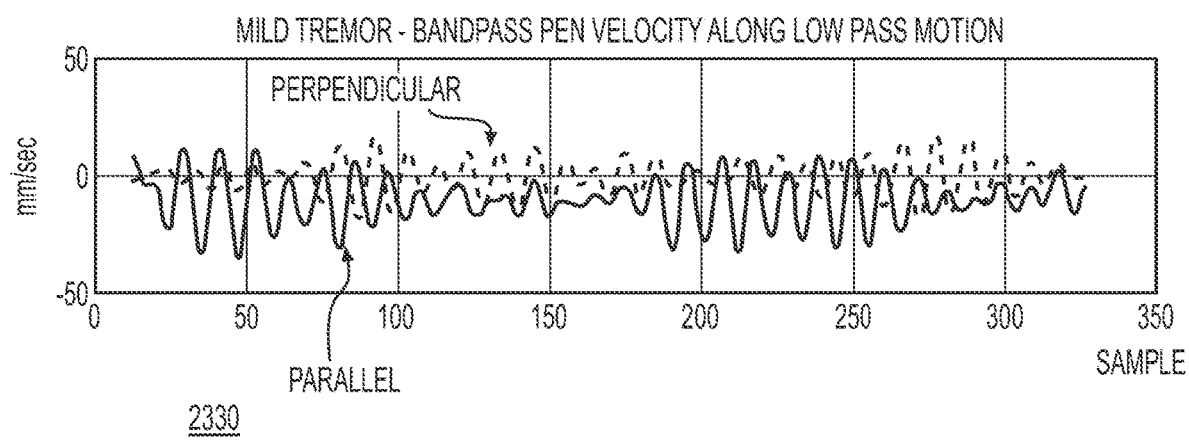
FIG. 21 depicts an example graph of tremor signals in a patient with Mild Tremor, in accordance with techniques presented herein.

The clock drawing of FIG. 19 illustrates a set of issues when judging presence of tremor in cases where the tremor is relatively mild. As shown in drawing 2100 of FIG. 19, by itself the clock drawing may not look particularly tremulous. However, as shown in FIGS. 20A-20D, plotting the low pass filtered clockface, and the bandpass velocity and acceleration reveals a tremor that is barely visible in FIG. 19. The low-pass filtering of the clockface enhances the tremor in FIG. 20A. The bandpass velocity curve in FIG. 20B shows oscillation in the speed of the pen (the distance to (0,0) keeps changing) that dwarfs the expected circular shape. The bandpass acceleration in FIG. 20C suggests erratic control of the pen. FIG. 21 at graph 2330 shows the bandpass velocity parallel and perpendicular to the direction of pen travel. Note the clear oscillatory tremor at around 7-8 Hz (there are about 7-8 oscillations in each 75 samples, which is a second of data.) This example clockface outline yielded a PnCurvLogEnergy score of 11.1, on the border of where one might put the threshold between normal and tremor.

Figure 22:
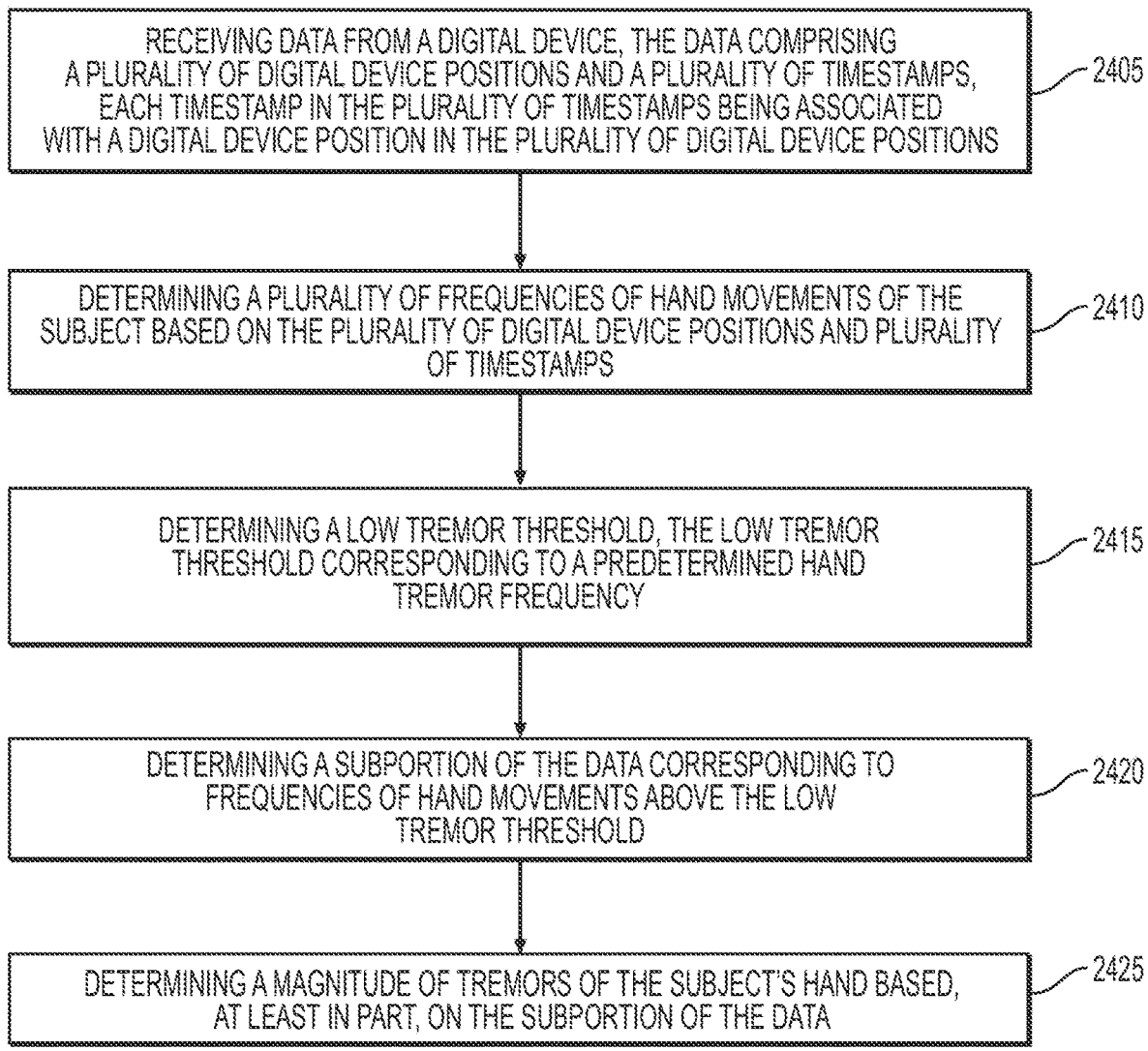
FIG. 22 is a block diagram of an exemplary method of measuring and quantifying tremor, according to an exemplary embodiment of the present disclosure.

FIG. 22 discloses an example block diagram 2400 of a technique presented herein. Step 2405 comprises receiving data from a digital device, the data comprising a plurality of digital device positions and a plurality of timestamps, each timestamp in the plurality of timestamps being associated with a digital device position in the plurality of digital device positions. At step 2410, a plurality of frequencies of hand movements of the subject may be determined based on the plurality of digital device positions and plurality of timestamps. At step 2415, a low tremor threshold may be determined, the low tremor threshold corresponding to a predetermined hand tremor frequency. At step 2420, a subportion of the data may be determined corresponding to frequencies of hand movements above the low tremor threshold. At step 2425, a magnitude of tremors of the subject's hand may be determined based, at least in part, on the subportion of the data.

Additional Techniques

Features discussed herein may be used to create tremor scores whose rating accuracy matches or exceeds that of medical professionals working from drawings on paper. One reason is that the telltale wavy lines drawn by a person with tremor make visible only the perpendicular component of velocity. With a digitizing pen, the system can achieve better performance because it can also measure oscillations in the direction of pen travel. This suggests that tremor rating by medical professionals might be improved by playing back a video of the patient drawing the picture. Erratic speed up and slow down of pen motion in the direction of travel may be nearly as visible as erratic pen motion perpendicular to travel. On the other hand, if the goal were to match the judgments of the medical professionals looking at static drawings, then it may be best to restrict the system to analyzing perpendicular components of velocity and acceleration.

The example features discussed earlier sum energy in the various filtered signals with equal weight to all samples summed. Alternative approaches are possible, such as assigning less weight to samples near the endpoints of the pen stroke, or using L1 norms or other measures.

Further, the algorithm might look at more than just the clockface outline stroke, processing any secondary strokes used to finish the clockface outline, plus perhaps strokes for the hour and minute hands. It may be desirable, however, to use only longer strokes in the analysis and algorithms.

It is also noted that, if accurate pressure measurements were available from the digitizing device, that normalization of the features might be adjusted according to pressure. This is because it is possible that more pressure might correspond to more highly stressed muscles which might increase tremor.

Techniques discussed herein may execute independently or coupled with the system that judges the cognitive impairment of the subject. Performance might be improved by using information about cognitive state to adjust thresholds or modify processing. For example, if the individual is believed to have dementia, then sudden changes in pen direction might be more likely caused by cognitive problems rather than tremor.

Further, the digitizing pen may compress lines that are mostly straight by dropping intermediate points. The interpolation scheme simply fills in points at uniform spacing along an exact line through the gap. The first derivative of the line in these interpolated sections may be constant and acceleration may be zero. This may distort the tremor quantification features. Fortunately, people with tremor tend not to move the pen in straight lines, so not many points will be interpolated. This anomaly may cause healthy subjects to have lower tremor scores than expected.

Also, a large set of healthy subjects may be used to get a better estimate of false alarm rate for the features. Expanding the range of data available should be possible as use of the digital clock test expands to more researchers.

In addition, techniques presented herein may further require drawing with the non-dominant and non-writing hand. Yet another possibility is that a screening or diagnostic system could be designed so that a high tremor score on the drawing test may trigger requests for additional drawings or other tests in order to refine the scores and improve accuracy.

Features of Embodiments

The digital version of the Clock Drawing Test may be augmented to measure tremor from the clockface and other stroke(s). Unlike existing techniques, the task may be very natural to the individual with their hand resting on the paper and drawing freehand on a sheet of paper. While the Clock Drawing Test is discussed herein, other drawing tests may be used. For example, pictures of other objects or faces, copied or traced or drawn from memory, spiral or pattern shapes, and others may all be used to measure tremor, for example from long strokes.

As discussed herein, if the goal is to match the ratings assigned by medical professionals observing the drawings, then measurements of motion perpendicular to the smoothed velocity vector may be used because these motions correspond closely to the features that are more easily observed by human vision. In addition, the deviation of the drawing from the intended shape, velocity, and acceleration may be measured. In particular, the tremor frequency band of 4-8 Hz may be given particular attention, while lower frequencies may be suppressed, as lower frequencies may be the result of voluntary motion. Frequencies higher than the 4-8 Hz band may similarly be suppressed.

Other techniques may be used in combination herein. For example, missing time-stamped pen coordinates or a non-uniform sampling may be resampled to a uniform sample rate through interpolation. Upsampling or downsampling might be used to adjust the digitizing device sampling rate. As discussed above, a variety of filter design algorithms, such as Parks-McClellan, least squares and linear programming, may be used. A variety of filter lengths may be used, especially if the sample rate is different than 75 Hz. The passband may also vary. If the digitizing pen has relatively low noise levels, then the bandpass filter could also be replaced by a high pass filter, keeping frequencies above 4 Hz or so.

Energy in bandpassed velocity and/or acceleration may be used to estimate tremor. A component of bandpassed velocity and/or acceleration, either at a fixed angle or perpendicular or parallel to pen motion, may be used to estimate tremor. If at a fixed angle, that angle may be selected in part by the subject's dominant hand, or by the positioning of the subject's fingers. The fixed angle may be estimated from the digital recording by, for example, finding the direction angle with greatest oscillatory energy.

Further, the tremor feature may be used to create a metric for subject screening for tremor. A tremor feature may also be created that mimics the tremor rating from human experts.

In addition, various transformations may be used such as a log-transform to ensure that the metric for subject screening for tremor has a specific distribution, for example, so that it matches ratings from human raters.

Tremor quantification metrics may be combined with other drawing process metrics, demographic information, and/or other cognitive testing results to improve the quantification of tremor and the screening and diagnosis of cognitive conditions.

Tremor quantification features may be used in a medical context for any of, for example, differential diagnosis of tremor predominant disorders (e.g. Essential Tremor) vs. secondary tremor (e.g. Parkinson's disease with tremor, dystonia with tremor, drug-induced tremor). Tremor features may further be used for monitoring and tracking tremor treatment for any change, or quantifying potential effects related to medical treatment such as medication or Deep Brain Stimulation. Tremor features may further be used to calibrate Deep Brain Stimulation to maximize the reduction in tremor or tremor-related symptoms, or for creating a score for the potential risk of falling, an event common amongst movement disorder individuals.

Further, tremor quantification features determined using techniques discussed herein may be used in an educational, vocational, and employment context for any of, for example, measuring the ability and risk of handling machinery, from equipment deemed dangerous (e.g. electric saw) to equipment requiring extreme motion precision by the user for the correct usage (e.g. circuit board soldering). Surgeons may also be tested and/or trained to ensure required level of precision. More generally, these techniques may be used for evaluating fine motor skills for prospective and current employment decisions.

Techniques disclosed herein thus are able to detect very subtle and mild tremor, and are able to do it much earlier in disease progression than conventional examination via the paper Clock Drawing Test. The magnitude of tremors may be determined, for example, by determining directional velocity and acceleration components of the tracked movements of a device held by the subject. Techniques disclosed herein may further be used to determine cognitive impairment. For at least these reasons, techniques disclosed herein improve the technical field.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for systems and methods for tremor detection and quantification through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A system for detecting tremors in a hand of a subject, the system comprising:
   a digital pen;
   an electronic device on which the subject makes a drawing using the digital pen,
   wherein at least one of the digital pen and the electronic device is configured to obtain a plurality of digital pen positions at a sampling rate of at least 75 times per second during the drawing,
   each digital pen position having x and y coordinates;
   a data storage device storing instructions for detecting tremors in the subject;
   and a processor configured to execute the instructions to perform a method including:
   receiving electronic data from at least one of the digital pen and the electronic device,
   the data comprising the plurality of digital pen positions and a plurality of timestamps,
   each timestamp in the plurality of timestamps being associated with a digital pen position in the plurality of digital pen positions;
   determining a plurality of frequencies of movements of the hand of the subject based on the plurality of digital pen positions and the plurality of timestamps;
   determining a subportion of the data corresponding to one or more frequencies of hand movements above a low tremor frequency threshold;
   and determining a magnitude of tremors of the hand of the subject based, at least in part, on the subportion of the data,
   wherein determining a magnitude of tremors of the hand of the subject based, at least in part, on the subportion of the data further comprises:
   determining a bandpass or high-pass filtered velocity signal by passing the subportion of the data through a bandpass or high-pass filter and a first derivative filter;
   determining low-pass filtered velocity data;

and determining the magnitude of tremors based, at least in part, on portions of the bandpass or high-pass filtered velocity signal that are perpendicular to the low-pass filtered velocity data;

wherein the sampling rate varies based on a velocity of the digital pen;

wherein the drawing is a clockface.

2. The system of claim 1, the method further comprising:
determining sections of the data received from the at least one of the digital pen and the electronic device with missing samples or a non-uniform sampling rate;
and resampling the data to a uniform sampling rate by interpolating one or more samples of missing position information based on the plurality of digital pen positions in the data.

3. The system of claim 1, the method further comprising:
determining low-pass data by passing the data through a low-pass filter;
and determining an estimate of a direction and a speed of the digital pen based, at least in part, on the low-pass data.

4. The system of claim 1, wherein determining a magnitude of tremors of the hand of the subject based, at least in part, on the subportion of the data further comprises:
determining a bandpass or high-pass filtered acceleration signal by passing the bandpass or high-pass filtered velocity signal through a second derivative filter;
and determining the magnitude of tremors of the hand of the subject based, at least in part, on an analysis of the bandpass or high-pass filtered velocity signal and the bandpass or high-pass filtered acceleration signal.

5. The system of claim 1, wherein at least one of the digital pen and the electronic device obtains one or more of an angle of the digital pen, a rotation of the digital pen, and a pressure applied by the digital pen, during the drawing.

6. The system of claim 1, the method further comprising:
determining one or more perimeter lines in a portion of the data corresponding to a perimeter of the clockface;
and determining the magnitude of tremors based, at least in part, on the one or more perimeter lines in the data.

7. A non-transitory computer readable medium for use on a computer system containing computer-executable programming instructions for performing a method for detecting tremors in a hand of a subject, the method comprising:
providing a digital pen and an electronic device on which the subject makes a drawing using the digital pen;
receiving electronic data from at least one of the digital pen and the electronic device,
the data comprising a plurality of digital pen positions and a plurality of timestamps,
each timestamp in the plurality of timestamps being associated with a digital pen position in the plurality of digital pen positions;
determining a plurality of frequencies of movements of the hand of the subject based on the plurality of digital pen positions and the plurality of timestamps;
determining a subportion of the data corresponding to one or more frequencies of movements above a low tremor frequency threshold;
determining a bandpass velocity signal by passing the subportion of the data through a bandpass filter and a first derivative filter;
normalizing the bandpass velocity signal by dividing by an average expected velocity, based on a length of time required to draw the drawing, and determining a magnitude of tremors of the hand of the subject based, at least in part, on an analysis of the normalized bandpass filtered velocity signal;

wherein at least one of the digital pen and the electronic device obtains the plurality of digital pen positions at a sampling rate of at least 75 times per second during the drawing;

wherein the sampling rate varies based on a velocity of the digital pen;

wherein the drawing is a clockface.

8. The computer readable medium of claim 7, the method further comprising:
determining sections of the data received from the at least one of the digital pen and the electronic device with missing samples or a non-uniform sampling rate;
and resampling the data to a uniform sampling rate by interpolating one or more samples of missing position information based on the plurality of digital pen positions in the data.

9. The computer readable medium of claim 7, the method further comprising:
determining low-pass data by passing the data through a low-pass filter;
and determining an estimate of a direction and a speed of the digital pen based, at least in part, on the low-pass data.

10. The computer readable medium of claim 7, wherein the electronic data includes pressure measurements from the digital pen, and normalizing the bandpass velocity signal is based on the pressure measurements.

11. The computer readable medium of claim 7, wherein the drawing includes a command clock and a copy clock.

12. The computer readable medium of claim 7, wherein the bandpass velocity signal is normalized based on a square of a ratio of ink length to the length of time required to draw the drawing.

13. The computer readable medium of claim 7, wherein the bandpass velocity signal is normalized based on a size of a bounding box and an average radius of the drawing.

14. A computer-implemented method for detecting tremors in a hand of a subject, comprising:
providing a digital pen and an electronic device on which the subject makes a drawing using the digital pen;
receiving electronic data from at least one of the digital pen and the electronic device,
the electronic data comprising a plurality of digital pen positions and a plurality of timestamps,
each timestamp in the plurality of timestamps being associated with a digital pen position in the plurality of digital pen positions;
determining a plurality of frequencies of movements of the hand of the subject based on the plurality of digital pen positions and the plurality of timestamps;
determining a subportion of the data corresponding to one or more frequencies of movements of the subject above a low tremor threshold and below a high tremor threshold;
determining a bandpass velocity signal by passing the subportion of the data through a bandpass filter and a first derivative filter,
normalizing the bandpass velocity signal by dividing by an average expected velocity, based on a length of time required to draw the drawing,
determining a magnitude of tremors of the hand of the subject based, at least in part, on an analysis of the normalized bandpass filtered velocity signal, and determining a degree of cognitive impairment of the subject based, at least in part, on the magnitude of tremors;
wherein at least one of the digital pen and the electronic device obtains the plurality of digital pen positions at a sampling rate of at least 75 times per second during the drawing;
wherein the sampling rate varies based on a velocity of the digital pen;
wherein the drawing is a clockface.

15. The computer-implemented method of claim 14, the method further comprising:
determining sections of the received data with missing samples or a non-uniform sampling rate;
and resampling the data to a uniform sampling rate by interpolating one or more samples of missing position information based on the plurality of digital pen positions in the data.

16. The computer-implemented method of claim 14, further comprising:
determining low-pass data by passing the data through a low-pass filter;
and determining an estimate of a direction and a speed of the digital pen based, at least in part, on the low-pass data.

17. The computer-implemented method of claim 14, wherein determining a magnitude of tremors of the hand of the subject based in part on the subportion of the data further comprises:
determining a bandpass or high-pass filtered velocity signal by passing the subportion of the data through a bandpass or high-pass filter and a first derivative filter;
and determining the magnitude of tremors of the hand of the subject based, at least in part, on an analysis of the bandpass or high-pass filtered velocity signal.

18. The computer-implemented method of claim 17, wherein determining a magnitude of tremors of the hand of the subject based in part on the subportion of the data further comprises:
determining a bandpass or high-pass filtered acceleration signal by passing the bandpass or high-pass filtered velocity signal through a second derivative filter;
and determining the magnitude of tremors of the hand of the subject based, at least in part, on an analysis of the bandpass or high-pass filtered velocity signal and the bandpass or high-pass filtered acceleration signal.

19. The computer-implemented method of claim 18, wherein the bandpass or high-pass filtered acceleration signal is normalized by dividing by an average acceleration.

20. The computer-implemented method of claim 17, wherein determining a magnitude of tremors of the hand of the subject based in part on the subportion of the data further comprises:
determining low-pass data by passing the data through a low-pass filter;
and determining the magnitude of tremors based, at least in part, on a portion of the bandpass or high-pass filtered velocity signal that is at a predetermined angle relative to the low-pass data.

21. The computer-implemented method of claim 14, wherein the data corresponds to the subject drawing the clockface, the method further comprising:
determining one or more perimeter lines in a portion of the data corresponding to a perimeter of the clockface;
and determining the magnitude of tremors based, at least in part, on the one or more perimeter lines in the data.

22. The computer-implemented method of claim 14, wherein the low tremor threshold is 4 Hz, and the high tremor threshold is 6 Hz.

* * * * *